US012274417B2

(12) United States Patent
Cooter et al.

(10) Patent No.: US 12,274,417 B2
(45) Date of Patent: Apr. 15, 2025

(54) ENDOSCOPE CONNECTOR AND ENDOSCOPE ADAPTER

(71) Applicant: Karl Storz SE & Co. KG, Tuttlingen (DE)

(72) Inventors: Anina Cooter, Goleta, CA (US); Michael Kloter, Sturbridge, MA (US); Evan M. Leingang, Plymouth, NM (US); Kevin R. Lochner, Maple Grove, MN (US); Indrek-Toomas Polluks, Rakvere (EE); Marko Radosevic, Goleta, CA (US); Jeremy Roth, Santa Barbara, CA (US); Reed O. Saunders, Minneapolis, MN (US); Thomas A. Tedham, Eden Prairie, MN (US); Richard A. Thompson, II, St. Louis Park, MN (US); Chase Van Rossen, Santa Barbara, CA (US)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 18/519,630

(22) Filed: Nov. 27, 2023

(65) Prior Publication Data
US 2024/0090748 A1 Mar. 21, 2024

Related U.S. Application Data

(62) Division of application No. 17/470,000, filed on Sep. 9, 2021, now Pat. No. 11,883,002.

(51) Int. Cl.
*A61B 1/00* (2006.01)
(52) U.S. Cl.
CPC ...... *A61B 1/00126* (2013.01); *A61B 1/00027* (2013.01); *A61B 1/00124* (2013.01); *A61B 1/00137* (2013.01)

(58) Field of Classification Search
CPC ............ A61B 1/00027; A61B 1/00114; A61B 1/00124; A61B 1/00126; A61B 1/00137
See application file for complete search history.

(56) References Cited

U.S. PATENT DOCUMENTS

| 4,574,783 A | 3/1986 | Kazuhiro et al. | |
| 4,855,819 A * | 8/1989 | Hibino | H04N 23/125 |
| | | | 348/E5.025 |

(Continued)

FOREIGN PATENT DOCUMENTS

| CN | 106235994 A | 12/2016 |
| EP | 1721568 A1 | 11/2006 |

(Continued)

OTHER PUBLICATIONS

Fujifilm "Eluxeo with Multi Light Technology—Discover Light Enhanced Endoscopy" FujiFilm Europe GmbH; Feb. 2021.

(Continued)

*Primary Examiner* — Aaron B Fairchild
(74) *Attorney, Agent, or Firm* — Jason H. Vick; Amped IP LLC

(57) ABSTRACT

A system includes an endoscope connector and an endoscope adapter. The endoscope connector includes a first portion. The first portion includes a first magnetic coupling element and a first planar portion that is perpendicular to an axial direction of the endoscope connector. The endoscope adapter includes a second planar portion. The second planar portion includes a second magnetic coupling element and a substantially planar surface that is perpendicular to an axial direction of the endoscope adapter. The endoscope connector is non-mechanically attachable to the endoscope adapter using the first magnetic coupling element and the second magnetic coupling element. The first planar portion is alignable with the second planar portion such that: electroconductive contacts of the endoscope connector are axially (Continued)

aligned with electroconductive pins of the endoscope adapter and a port of the endoscope connector is axially aligned with a corresponding insertion port of the endoscope adapter.

18 Claims, 19 Drawing Sheets

(56) References Cited

U.S. PATENT DOCUMENTS

| | | | |
|---|---|---|---|
| 4,974,075 A | | 11/1990 | Nakajima |
| 5,343,855 A | * | 9/1994 | Iida ............................ A61B 1/12 |
| | | | 600/157 |
| 6,348,035 B1 | | 2/2002 | Takami |
| 7,361,140 B2 | | 4/2008 | Ries et al. |
| 7,641,610 B2 | | 1/2010 | Nakamura et al. |
| 8,177,560 B2 | | 5/2012 | Rohrbach et al. |
| 8,576,034 B2 | | 11/2013 | Bilbrey et al. |
| 9,833,127 B2 | | 12/2017 | Tomatsu et al. |
| 11,298,003 B2 | | 4/2022 | Duckett, II et al. |
| 2009/0287047 A1 | | 11/2009 | Onoda et al. |
| 2012/0202385 A1 | * | 8/2012 | Miyagi .............. A61B 1/00128 |
| | | | 439/626 |
| 2013/0035550 A1 | | 2/2013 | Watanabe et al. |
| 2016/0128549 A1 | | 5/2016 | Juergens |
| 2017/0215702 A1 | | 8/2017 | Niwa et al. |
| 2017/0347862 A1 | | 12/2017 | Yasunaga |
| 2018/0000323 A1 | | 1/2018 | Niwa et al. |
| 2018/0206884 A1 | | 7/2018 | Beaupre |
| 2020/0187758 A1 | | 6/2020 | Duckett, III et al. |
| 2023/0074215 A1 | | 3/2023 | Cooter et al. |

FOREIGN PATENT DOCUMENTS

| | | |
|---|---|---|
| EP | 1985225 B1 | 12/2010 |
| EP | 1752082 B1 | 3/2011 |
| EP | 1990871 B1 | 6/2012 |
| EP | 2548499 A1 | 1/2013 |
| EP | 2478825 B1 | 8/2015 |
| EP | 1645219 B1 | 11/2016 |
| EP | 3152274 A1 | 5/2017 |
| EP | 3184028 A1 | 6/2017 |
| EP | 1430344 B1 | 7/2017 |
| JP | 2005-192753 A | 7/2005 |
| JP | 6147444 B2 | 6/2017 |
| WO | WO 2015/000554 A1 | 1/2015 |
| WO | WO 2018/040772 A1 | 3/2018 |

OTHER PUBLICATIONS

Karl Storz—Endoskope "Instruction Manual—Silver Scope® Video Duodenoscopes, Models 13885NKS, 13885PKS" Version 2.1; Jan. 2020.
Olympus America Inc. "Evis Exera III—Advancing the Art of Endoscopy" Date Unknown.
Olympus America Inc. "Evis Exera III—Advancing Workflow" Available at https://medical.olympusamerica.com/products/evis-exera-endoscopy/workflow; printed May 31, 2021.
German Office Action for corresponding German Patent Application No. 10 2021 123 315.1, mailed Jun. 22, 2022.
European Search Report for European Patent Application No. 22194580.1, mailed Feb. 3, 2023.
Office Action for (Restriction Requirement) for U.S. Appl. No. 17/470,000, mailed May 30, 2023.
Office Action for U.S. Appl. No. 17/470,000, mailed Aug. 31, 2023.
Notice of Allowance for U.S. Appl. No. 17/470,000, mailed Dec. 4, 2023.
U.S. Appl. No. 29/930,914, filed Mar. 4, 2021, Cooter et al.

* cited by examiner

ENDOSCOPE CONNECTOR AND ENDOSCOPE ADAPTER

CROSS-REFERENCE TO RELATED APPLICATIONS

This application is a Divisional of U.S. patent application Ser. No. 17/470,000, filed Sep. 9, 2021, now U.S. Pat. No. 11,883,002. The entire contents of which are incorporated herein by reference in their entirety.

FIELD

The present disclosure is generally directed to devices and systems for imaging an anatomy.

BACKGROUND

Some medical equipment may support imaging an anatomy (e.g., a human anatomy). For example, some medical equipment may support procedures such as an endoscopy to diagnose and/or treat conditions that affect organs (e.g., esophagus, stomach, duodenum) of a body of a patient. In some medical equipment, an instrument such as an endoscope may be used with various other medical equipment (e.g., video processors, light sources, fluid/gas sources, surgical equipment, etc.) associated with performing such procedures.

SUMMARY

The following is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. Any one or more of these features can be used in combination with any one or more of the other features disclosed herein including but not limited to the following.

Exemplary aspects are directed to an endoscope connector, including: a first portion having a first shape, the first portion including: a planar portion provided on at least a portion of the first shape, the planar portion including a substantially planar surface that may be parallel to an axial direction of the endoscope connector; and a first substantially planar surface perpendicular to the axial direction of the endoscope connector. The endoscope connector includes a first port protruding through the first planar surface. In some aspects, the first port may be a light port. The endoscope connector includes a second port protruding through the first planar surface. In some aspects, the second port may be an insufflation port. The endoscope connector includes a second portion having a circular shape, the second portion including: a second substantially planar surface perpendicular to the axial direction the endoscope connector; and a set of electroconductive contacts at least partially protruding through the second substantially planar surface. In some aspects, the set of electroconductive contacts are axially aligned with respect to the axial direction of the endoscope connector.

Optional aspects of the endoscope connector include wherein the planar portion is alignable with a corresponding planar portion of an external apparatus such that: the set of electroconductive contacts are axially aligned with a set of electroconductive pins of the external apparatus; and at least one port of the endoscope connector is axially aligned with a corresponding insertion port of the external apparatus.

Optional aspects of the endoscope connector include wherein the second portion includes a third portion including the second substantially planar surface; and at least a portion of each electroconductive contact of the set of electroconductive contacts is sealed in the third portion using a sealing element.

Optional aspects of the endoscope connector include wherein the sealing element includes at least one of: an O-ring seal; an adhesive material; a ceramic material; a glass material; a rubber material; and a urethane material.

Optional aspects of the endoscope connector include wherein at least a portion of the first substantially planar surface, at least a portion of the second substantially planar surface, or both, is substantially smooth.

Optional aspects of the endoscope connector include wherein the endoscope connector is non-mechanically attachable to an external apparatus.

Optional aspects of the endoscope connector include wherein the first portion includes at least one magnetic coupling element.

Optional aspects of the endoscope connector include wherein at least a portion of the first substantially planar surface includes the at least one magnetic coupling element.

Aspects of the above endoscope connector include wherein at least a portion of the first substantially planar surface covers an end of the at least one magnetic coupling element.

Optional aspects of the endoscope connector include wherein the at least one magnetic coupling element is included in the first portion using insert injection molding; the at least one magnetic coupling element is sealed within the first portion using an O-ring seal; or both.

Optional aspects of the endoscope connector include wherein the at least one magnetic coupling element includes a ferromagnetic material.

Optional aspects of the endoscope connector include wherein the at least one magnetic coupling element includes a magnet.

Optional aspects of the endoscope connector include wherein the at least one magnetic coupling element includes an electromagnet.

Optional aspects of the endoscope connector include wherein the first port extends parallel to the axial direction of the endoscope connector; the second port extends parallel to the axial direction of the endoscope connector; and at least one dimension of the second port is smaller than a corresponding dimension of the first port.

Optional aspects of the endoscope connector include wherein the set of electroconductive contacts are electrically conductive with a set of electrically conductive pins of an external apparatus.

Optional aspects of the endoscope connector include wherein the set of electroconductive contacts are of a same shape; and the set of electroconductive contacts are spaced apart from one another according to a fixed distance.

Optional aspects of the endoscope connector include wherein the endoscope connector communicates data with an external apparatus via at least one first electroconductive contact of the set of electroconductive contacts; and the endoscope connector receives power from the external apparatus via at least one second electroconductive contact of the set of electroconductive contacts.

Optional aspects of the endoscope connector include wherein the first shape includes: a circular shape; a polygonal shape; a squircular shape; or a combination thereof.

Exemplary aspects are directed to an endoscope adapter, including: at least one magnetic coupling element; and a first substantially planar surface covering an end of the at least one magnetic coupling element. In some aspects, the substantially planar surface is perpendicular to an axial direction of the endoscope adapter. The endoscope adapter includes a second substantially planar surface perpendicular to the axial direction of the endoscope adapter. The endoscope adapter includes a set of electroconductive pins protruding through the second substantially planar surface. In some aspects, the set of electroconductive pins are axially aligned with respect to the axial direction of the endoscope adapter.

Optional aspects of the endoscope adapter include a planar portion including a substantially planar surface that is parallel to the axial direction of the endoscope adapter. In some aspects, the planar portion is alignable with a corresponding planar portion of an endoscope connector such that: the set of electroconductive pins are axially aligned with a set of electroconductive contacts of the endoscope connector; and at least one insertion port of the endoscope adapter is axially aligned with a corresponding port of the endoscope connector.

Optional aspects of the endoscope adapter include a planar portion including a third substantially planar surface that is perpendicular to the axial direction of the endoscope adapter. In some aspects, a first distance between the first substantially planar surface and a distal end of the endoscope adapter is different from a second distance between the third substantially planar surface and the distal end.

Optional aspects of the endoscope adapter include a second set of second electroconductive pins protruding through the second substantially planar surface. In some aspects, the set of second electroconductive pins are axially aligned with respect to the axial direction of the endoscope adapter; and a first distance between at least one electroconductive pin of the set of electroconductive pins and a central axis of the endoscope adapter is different from a second distance between at least one second electroconductive pin of the set of second electroconductive pins and the central axis of the endoscope adapter.

Optional aspects of the endoscope adapter include wherein the set of electroconductive pins produce a force that is opposite an attraction force associated with the at least one magnetic coupling element. In some aspects, the force produced by the set of electroconductive pins and the attraction force associated with the at least one magnetic coupling element are parallel to the axial direction of the endoscope adapter.

Optional aspects of the endoscope adapter include wherein the endoscope adapter is non-mechanically attachable to an endoscope connector.

Optional aspects of the endoscope adapter include a first insertion port and a second insertion port. In some aspects, a diameter of the first insertion port is perpendicular to the axial direction of the endoscope adapter. In some aspects, a diameter of the second insertion port is perpendicular to the axial direction of the endoscope adapter. In some aspects, the diameter of the second insertion port is smaller than the diameter of the first insertion port.

Optional aspects of the endoscope adapter include wherein light emitted by a light source is communicable via the first insertion port; and fluid provided by a fluid source is communicable via the second insertion port. In some aspects, the set of electroconductive pins are electrically conductive with a set of electroconductive contacts of an endoscope connector.

Optional aspects of the endoscope adapter include wherein the set of electroconductive pins are of a same shape; and the set of electroconductive pins are spaced apart from one another according to a fixed distance.

Optional aspects of the endoscope adapter include wherein the endoscope adapter communicates data with an endoscope connector via at least one first electroconductive pin of the set of electroconductive pins; and the endoscope adapter transmits power to the endoscope connector via at least one second electroconductive pin of the set of electroconductive pins.

Optional aspects of the endoscope adapter include wherein the at least one magnetic coupling element includes a magnet.

Optional aspects of the endoscope adapter include wherein the at least one magnetic coupling element includes an electromagnet.

Optional aspects of the endoscope adapter include wherein the at least one magnetic coupling element includes a ferromagnetic material Exemplary aspects are directed to a system including: an endoscope connector including a first portion having a first shape, the first portion including: a first planar portion that is parallel to an axial direction of the endoscope connector; and at least one first magnetic coupling element. The system includes an endoscope adapter including a second planar portion, the second planar portion including: a substantially planar surface that is parallel to an axial direction of the endoscope adapter; and at least one second magnetic coupling element. In some aspects, the endoscope connector is non-mechanically attachable to endoscope adapter using the at least one first magnetic coupling element and the at least one second magnetic coupling element.

Optional aspects of the system include wherein the first planar portion is alignable with the second planar portion such that: a set of electroconductive contacts of the endoscope connector are axially aligned with a set of electroconductive pins of the endoscope adapter; and at least one port of the endoscope connector is axially aligned with a corresponding insertion port of the endoscope adapter.

Optional aspects of the system include wherein the at least one first magnetic coupling element includes a ferromagnetic material; and the at least one second magnetic coupling element includes at least one magnet.

Optional aspects of the system include wherein the at least one first magnetic coupling element includes at least one first magnet; and the at least one second magnetic coupling element includes at least one second magnet.

Optional aspects of the system include wherein the at least one first magnetic coupling element includes at least one first magnet; and the at least one second magnetic coupling element includes at least one second magnet.

Optional aspects of the system include a light source. In some aspects, light generated by the light source is communicable over a first input port included in the endoscope connector.

Optional aspects of the system include a fluid source. In some aspects, fluid output from the fluid source is communicable over a second input port included in the endoscope connector.

Optional aspects of the system include a video processor. In some aspects, signals are communicable to the video processor over a set of electroconductive contacts of the endoscope connector and a set of electroconductive pins of the endoscope adapter.

Optional aspects of the system include a first apparatus including the light source; and a second apparatus including the video processor.

Optional aspects of the system include an apparatus including the light source and the video processor.

Optional aspects of the endoscope connector, endoscope adapter, and/or system include:

It is to be appreciated that any one or more of the above optionally disclosed aspects can be claimed alone or in combination with any other optional aspect as substantially disclosed herein.

Additionally, it is to be appreciated that any one or more of the above optionally disclosed aspects can be claimed as substantially disclosed herein, optionally in combination with any one or more other aspects as substantially disclosed herein, regardless of the embodiment the aspect is disclosed in association with.

This disclosure also encompasses and expressly includes one or means adapted to perform any one or more of the above aspects as substantially disclosed herein.

This disclosure also encompasses and expressly includes use of any one or more of the aspects or features as disclosed herein.

It is to be appreciated that any feature described herein can be claimed in combination with any other feature(s) as described herein, regardless of whether the features come from the same described implementation.

It is to be appreciated that any feature described herein may be implemented as an optional feature. In some aspects, it is to be appreciated that any feature described herein may be omitted. In some aspects, it is to be appreciated that any feature described herein may be combined with any other feature(s) described herein.

Numerous additional features and advantages of the above endoscope connector, endoscope adapter, and/or system are described herein and will be apparent to those skilled in the art upon consideration of the following Detailed Description and in view of the figures.

DETAILED DESCRIPTION

Figure 1A:
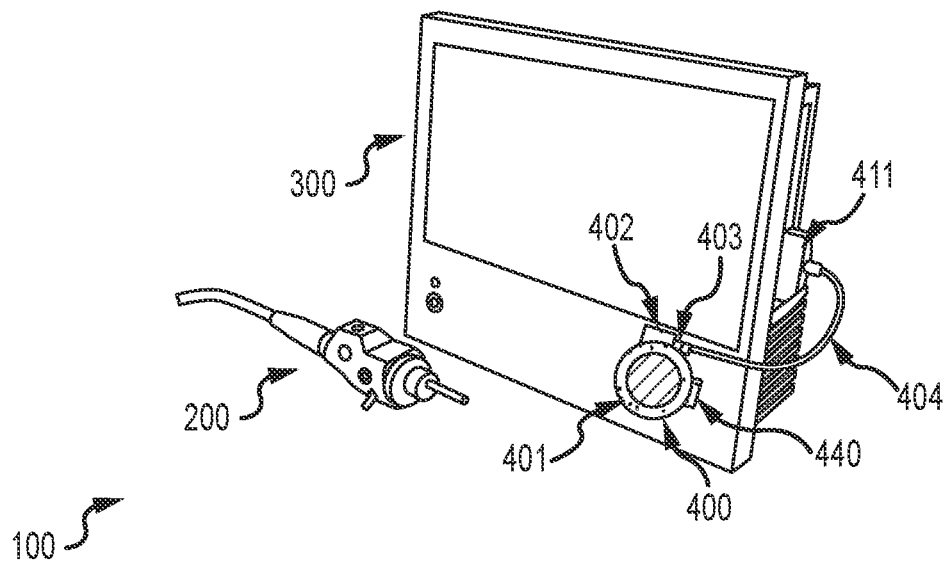
FIGS. 1A, 1B, and 1C illustrate examples of a system in accordance with aspects of the present disclosure.

Before any example aspects of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides example aspects, features, and implementations, and is not intended to limit the scope, applicability, or configuration of the claims. Rather, the ensuing description will provide those skilled in the art with an enabling description for implementing the described example aspects, features, and implementations. It being understood that various changes may be made in the function and arrangement of elements without departing from the spirit and scope of the appended claims.

Various aspects of the present disclosure will be described herein with reference to drawings that may be schematic illustrations of idealized configurations.

Medical equipment may support procedures for examining the interior of organs or cavities of a body (e.g., a human body, an animal body, etc.) using an instrument such as an endoscope, a gastroscope, a colonoscope, or the like. In some medical equipment, a corresponding receptacle supportive of interconnection with the instrument and an external apparatus (e.g., a video processor) does not include electrical contacts supportive of communicating signals with the instrument. For example, such receptacles may support a light source and a fluid connection, without supporting the communication of video data. In some cases, a separate video cable may be provided to communicate video signals between the instrument (e.g., endoscope, a gastroscope, a colonoscope) and the corresponding or an additional external apparatus, which may be cumbersome. For example, the video cable may have a relatively high degree of freedom of movement (e.g., the video cable may shake or otherwise move in an axial and/or radial direction). Accordingly, for example, in some medical equipment, an endoscope is connected to a light source for light and fluid, and a video cable is a separate connection between the endoscope and an additional camera control unit (CCU).

Some medical equipment may implement a spring ring as a locking mechanism for attaching an endoscope connector to the apparatus, while minimizing undesired movement of the connection. However, variation in the shape of the spring ring may vary due to manufacturing tolerances and/or conditions, and ensuring a consistent and/or desired locking force of the locking mechanism may be relatively difficult. Some spring ring designs incorporate one or more grooves (e.g., visually hidden grooves) for improving the locking force. However, such grooves may introduce other drawbacks associated with dirt accumulation within the grooves. Additionally, in some cases, user error and/or user carelessness may result in the endoscope connector being attached incorrectly.

According to example aspects of the present disclosure, an endoscope connector and endoscope adapter (also referred to herein as an endoscope adapter, a GI adapter, a colonoscope adapter, a duodenoscope adapter, or a GI receptacle) are described that support improved usability and connectability of an endoscope and the endoscope adapter. In some aspects, a connection system is described that supports a reduced number of connections between the endoscope connector and the endoscope adapter, reduced forces associated with inserting the endoscope connector into the endoscope adapter (e.g., insertion force), reduced forces associated with disconnecting the endoscope connector and the endoscope adapter (e.g., disconnection force), and improved cable management. In some cases, aspects of the endoscope adapter described herein may support mechanical compatibility with equipment different from the endoscope connector (e.g., the endoscope adapter described herein may be mechanically compatible with other gastroscopes and colonoscopes, or the like).

In some aspects, the endoscope adapter described herein may support improved ergonomics of equipment setup by combining cable connection with scope connection task. For example, aspects of the endoscope connector and GI adapter may support power and signal interconnectivity between an endoscope and a CCU by integrating power and signal interconnection cables (e.g., video endoscope adapter (VEA) cables) into the endoscope adapter. Accordingly, for example, aspects of the present disclosure may support the communication of video signals, data, light, and fluid (e.g., gas, water, etc.) between an endoscope and an endoscope adapter, using a single cable. For example, aspects of the present disclosure may provide an improvement (e.g., reduced cost, reduced service burden) compared to other medical equipment in which a cable is used for light and fluid and another cable is used for data signals and non-data signals. In some aspects, examples of assembly material, electrical contacts and geometries described herein with reference to the endoscope connector and the endoscope adapter may support high speed video data (e.g., data communications of 4 Gbps or higher).

Figure 1B:
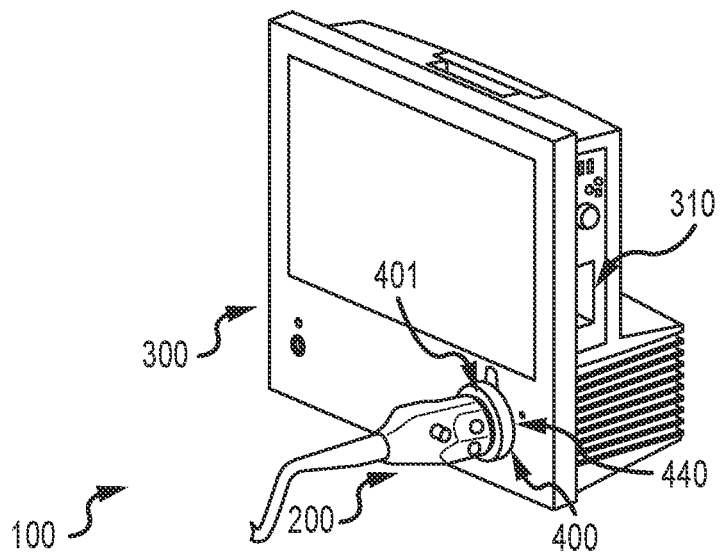
Figure 1C:
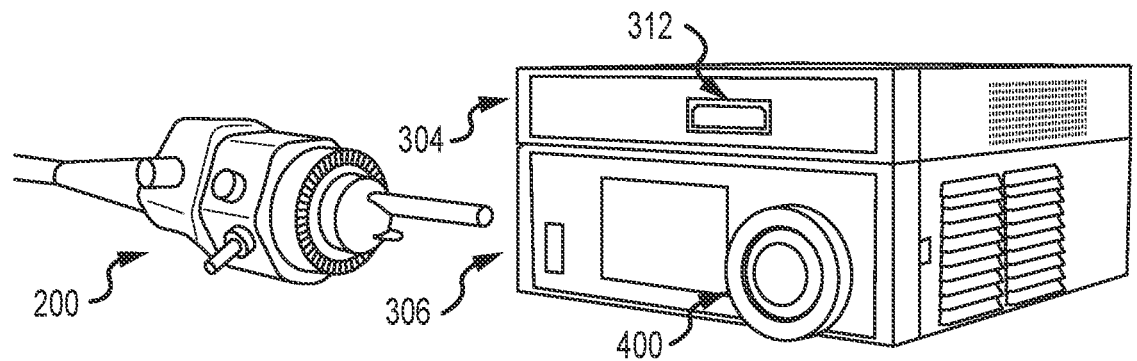

FIGS. 1A, 1B, and 1C illustrate examples of a system 100 in accordance with aspects of the present disclosure.

Referring to the example of FIG. 1A, the system 100 may include an endoscope connector 200, an external apparatus 300-a, and an endoscope adapter 400 (also referred to herein as an endoscope receptacle, a gastro intestinal (GI) adapter). The external apparatus 300 may include medical equipment supportive of medical, diagnostic, and treatment of a subject (e.g., endoscopic diagnosis and treatment of a human subject). The external apparatus 300 may include a video processor (also referred to herein as a camera control unit (CCU)), a light source, and a fluid/gas source. In some aspects, the fluid/gas source may be an insufflator or a pump inside the external apparatus 300. For example, the fluid/gas source may be a container (e.g., a bottle) including a gas or water. In the example of FIG. 1A, the external apparatus 300 includes an integrated display.

The GI adapter 400 may support interconnection (e.g., electro-mechanical and/or electro-optical and/or optical and/or fluid coupling) between the external apparatus 300 and the endoscope connector 200. Optionally or alternatively, the endoscope adapter 400 may support interconnection (e.g., mechanical coupling) between the external apparatus 300 and other endoscope connectors, gastroscope connectors, and/or colonoscope connectors.

Aspects described herein of the endoscope connector 200 and GI adapter 400 may support the communication of data signals (e.g., video signals), non-data signals (e.g., power), light, and fluid (e.g., gas, water, etc.) between an endoscope, the endoscope connector 200, the endoscope adapter 400, and the external apparatus 300, for example, using a single cable. For example, aspects of the present disclosure may provide an improvement (e.g., reduced cost, reduced service burden) compared to other medical equipment in which a cable is used for light and fluid and another cable is used for data signals and non-data signals). Example aspects of the external apparatus 300 and the endoscope adapter 400 are later described herein.

In some aspects, the external apparatus 300 may include executable software applications and/or hardware capable of recognizing (correct/incorrect) insertion of the endoscope connector 200 at the endoscope adapter 400. In some cases, the external apparatus 300 may include executable software applications and/or hardware capable of controlling magnetic forces associated with electrically and non-mechanically coupling the endoscope connector 200 to the endoscope adapter 400, aspects of which are later described herein.

Referring to the example of FIG. 1A, the endoscope adapter 400 may include a receptacle portion 401, an insulator 402, a distal nut 403, a cable core 404, a proximal connector 411 (also referred to herein as a cable connector), and a plug holder 440, aspects of which are later described with reference to FIG. 4. In some aspects, one or more portions of the endoscope adapter 400 (e.g., receptacle portion 401, insulator 402, distal nut 403, plug holder 440, etc.) may be any shape or form. For example, one or more portions of the endoscope adapter 400 (e.g., receptacle portion 401, insulator 402, distal nut 403, plug holder 440, etc.) may be circular shaped, polygonal shaped, squircular shaped, cylindrical shaped, or any combination thereof.

Referring to the example of FIG. 1B, an optional and/or alternative implementation of the external apparatus 300 and the endoscope adapter 400 are illustrated, example aspects of which are later described herein. For example, the endoscope adapter 400 may include the receptacle portion 401 and the plug holder 440, while omitting other features (e.g., insulator 402, distal nut 403, cable core 404, proximal connector 411) thereof, aspects of which are later described with reference to FIG. 4.

Referring to the example of FIG. 1C, in an optional and/or alternative implementation, the system 100 may include an external apparatus 304 (e.g., including a video processor) and an external apparatus 306 (e.g., including a light source and/or a fluid source) which, in combination, support the features of the external apparatus 300.

Portions of the endoscope connector 200 and the endoscope adapter 400 may have mutually complementary shapes, aspects of which are described herein. Example aspects of the endoscope connector 200, the external apparatus 300 (or apparatuses 300), and the endoscope adapter 400 are described herein with respect to the following figures.

In the figures that follow, example features of the endoscope connector 200 and endoscope adapter 400 are described in conjunction with a coordinate system 102. For example, in FIGS. 2A, 2B, 2C, 3A, 3B, 4, 5A, 5B, 6, 7A, 7B, 8A, 8B, 8C, 9A, and 9B that follow, example features and components (e.g., with respect to dimensions, positions, spacing, directionality, etc.) of the endoscope connector 200 and endoscope adapter 400 are defined with respect to an X-axis, a Y-axis, and a Z-axis of the coordinate system 102.

Figure 2A:
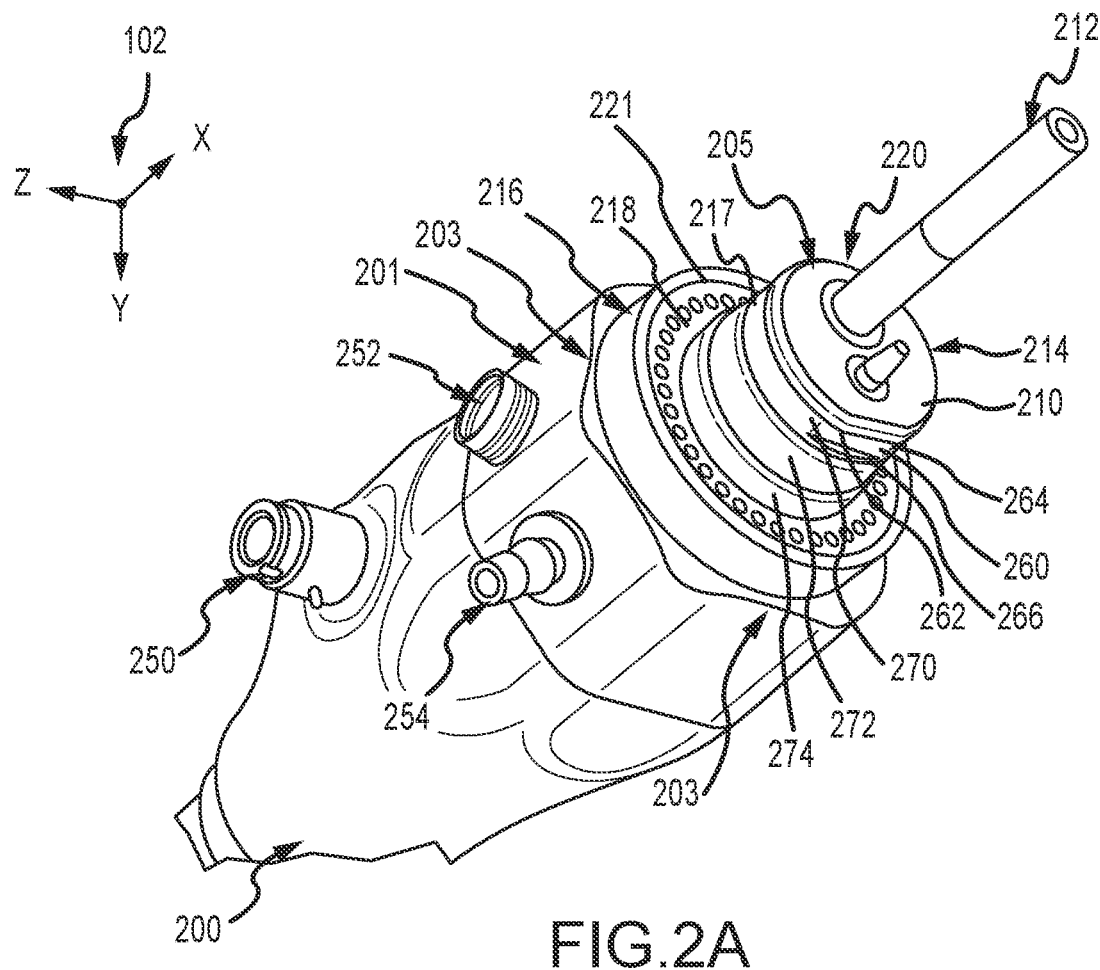
FIGS. 2A and 2B are perspective views of an endoscope connector in accordance with example aspects of the present disclosure.
Figure 2B:
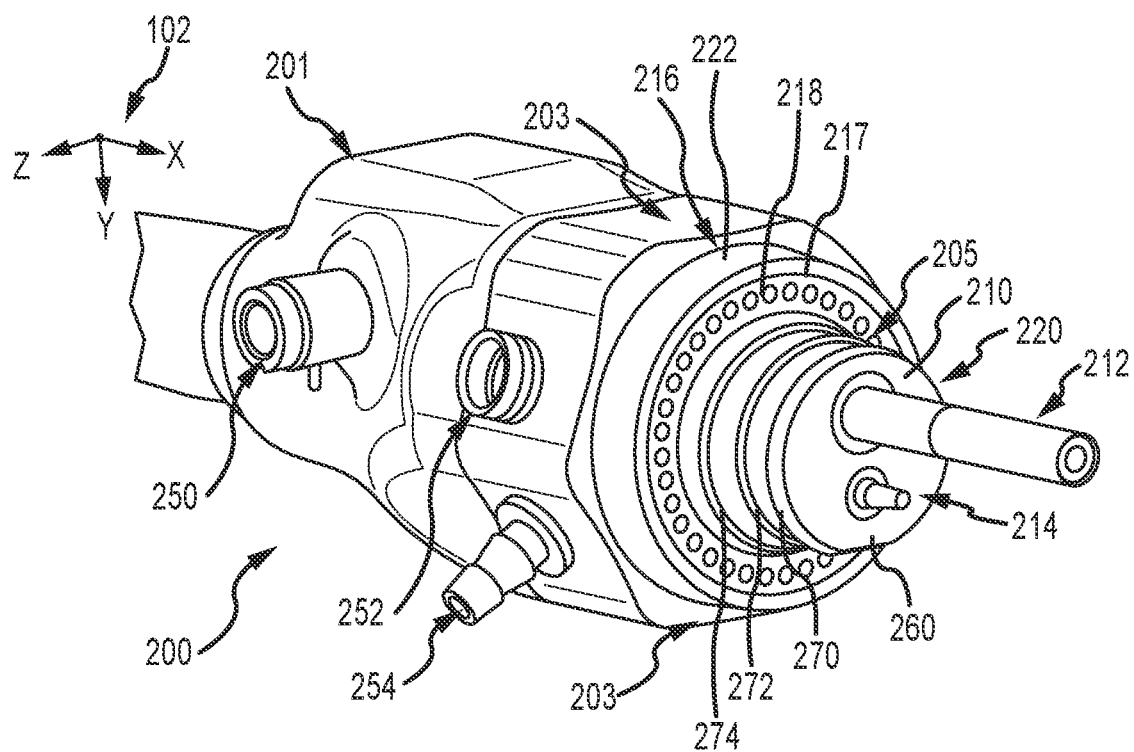
Figure 2C:
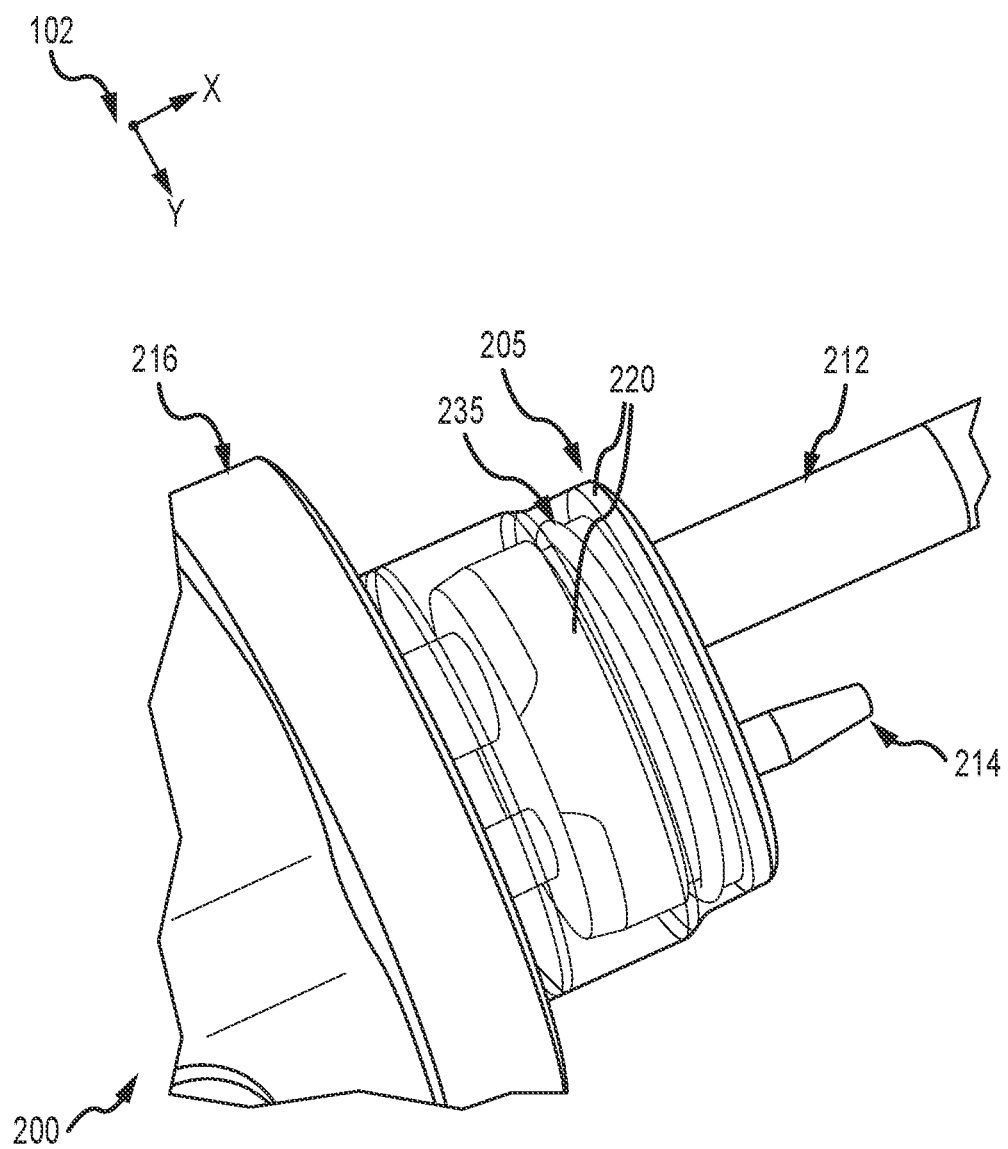
FIG. 2C is a partially transparent perspective view of an endoscope connector in accordance with example aspects of the present disclosure.

FIGS. 2A and 2B are perspective views of the endoscope connector 200 in accordance with example aspects of the present disclosure. FIG. 2C is a partially transparent perspective view of an endoscope connector in accordance with example aspects of the present disclosure.

With reference to the coordinate system 102, an axial direction described herein of the endoscope connector 200 is along the endoscope connector 200, corresponds with an insertion direction associated with the endoscope connector 200, and may be defined as a dimension along the X-axis.

According to example aspects of the present disclosure, an endoscope connector 200 may include a connector case 201 provided on a proximal end side of the endoscope connector 200 and a plug section 205 (also referred to herein as a plug, a nose, or a first portion of the endoscope connector 200) provided on the distal end side of the endoscope connector 200.

The connector case 201 may include a set of ports (e.g., port 250, port 252, port 254). For example, the connector case 201 may include a port 250 (e.g., a connection port for leakage testing), a port 252 (e.g., a water bottle connection port), and a port 254 (e.g., a suction/aspiration port) installed on the connector case 204.

The plug section 205 may be circular shaped. Optionally or alternatively, the plug section 205 may be polygonal shaped. Optionally or alternatively, the plug section 205 may be squircular shaped (e.g., be formed of a combination of a circular shape and a square shape). Optionally or alternatively, the plug section 205 may be cylindrically shaped. In some aspects, the plug section 205 may include any combination of shapes (e.g., circular, polygonal, squircular, cylindrical). According to example aspects of the present disclosure, the shape of the plug section 205 may support insertion of the plug section 205 inside of an inner shape (e.g., receiving portion 405) of the endoscope adapter 400, aspects of which are described later herein.

The plug section 205 may include a single or multiple planar surfaces (e.g., planar surface 260, planar surface 262, planar surface 264, etc.). In some aspects, a portion or an entirety of each planar surface 260, planar surface 262, and planar surface 264 may be substantially planar. In some aspects, the planar surface 260, planar surface 262, and planar surface 264 (individually, or in combination) may be referred to as a planar portion. In an example, the planar portion may include a planar surface (e.g., any of planar surface 260 through planar surface 264) that is parallel to an axial direction (e.g., X-axis) of the endoscope connector 200. For example, the planar surface 260 extends in the axial direction (e.g., X-axis) of the endoscope connector 200 and in a direction (e.g., along the Z-axis) that is perpendicular the axial direction (e.g., X-axis).

According to example aspects of the present disclosure, the planar surface 260 may be a flat surface supportive of minimizing rotational movement of the plug section 205 (and endoscope connector 200) with respect to the axial direction of the endoscope connector 200. In an example, the planar surface 262 may be a curved surface, the planar surface 264 may be a curved surface, and the planar surface 262 and planar surface 264 may have a same curvature.

In another example, the planar surface 260 through the planar surface 264 may each be a flat surface. In some aspects, the planar surface 260 may have a length (in a direction (e.g., Z-axis) perpendicular to the axial direction (e.g., X-axis) of the endoscope connector 200) different from a respective length of at least one of the planar surface 262 and the planar surface 264. Optionally or alternatively, the planar surface 260 may have a length equal to a respective length of at least one of the planar surface 262 and the planar surface 264. In some aspects, the planar surface 260 through the planar surface 264 may be equal in width (in the axial direction (e.g., X-axis) of the endoscope connector 200).

The plug section 205 may include a planar surface 266. In some aspects, the planar surface 266 may be perpendicular to an axial direction (e.g., X-axis) of the endoscope connector 200. For example, the planar surface 266 may extend in directions (e.g., Y-axis and Z-axis) perpendicular to the axial direction (e.g., X-axis) of the endoscope connector 200. The planar surface 266 may be substantially planar.

The plug section 205 may include additional substantially planar surfaces (e.g., substantially planar surface 270, substantially planar surface 272, and substantially planar surface 274). In some aspects, the diameters of the planar surface 270, planar surface 272, planar surface 274 with respect to the axial direction of the endoscope connector 200 may be different from or equal to one another. For example, the diameter of the planar surface 270 may have a first value d1, the diameter of the planar surface 272 may have a second value d2, and the diameter of the planar surface 274 may have a third value d3. In the example illustrated in FIGS. 2A and 2B, d1 is smaller than d2, and d2 is smaller than d3. Optionally or alternatively (not illustrated), d1, d2, and d3 may be equal to one another.

In some aspects, the heights of the planar surface 270, planar surface 272, planar surface 274 (e.g., in the axial direction (e.g., X-axis) of the endoscope connector 200 (i.e., in a direction parallel to the axial direction) may be different from or equal to one another. For example, the height of the planar surface 270 may have a first value h1, the height of the planar surface 272 may have a second value h2, and the height of the planar surface 274 may have a third value h3.

The plug section 205 may include a coupling element 220. In an example, the coupling element 220 may be a magnetic coupling element formed of a ferromagnetic material (e.g., corrosion resistant stainless steel). In some aspects, the coupling element 220 may be attached/integrated into the plug section 205 using insert injection molding (e.g., illustrated at FIGS. 2C and 9A). In some other aspects, the coupling element 220 is sealed in the plug section 205 using an O-ring seal(s) 235 (e.g., illustrated at FIGS. 2C, 7A, and 7B).

Optionally or alternatively, the coupling element 220 may be a non-magnetic coupling element (e.g., formed of a non-ferromagnetic material). For example, the plug section 205 may include one or more magnets 231 (e.g., a magnet 231-$a$ and a magnet 231-$b$). In an example, the one or more magnets 231 may be integrated within the coupling element 220 (e.g., as illustrated at FIG. 9B). In an example aspect, the magnets 231 may be permanent magnets (e.g., neodymium magnets). In some aspects, the magnets 231 may have an outer diameter (perpendicular to the axial direction (e.g., X-axis) of the endoscope connector 200) of 0.375 inches and a length (in the axial direction (e.g., X-axis) of the endoscope connector 200) of 0.500 inches.

Optionally or alternatively, the magnets 231 may be electromagnets (e.g., including a core of magnetic material such as iron) which may be magnetized in response to an electric current. In some cases, an endoscope, the endoscope connector 200, and/or an external apparatus 300 described herein may include a user interface (e.g., a switch, a button, a touch screen, etc.) for activating the electric current (e.g., for magnetizing the magnets 231).

The coupling element 220 may have a substantially planar surface 210 perpendicular to the axial direction (e.g., X-axis) of the endoscope connector 200. For example, the substantially planar surface 210 may extend in directions (e.g., Y-axis and Z-axis) perpendicular to the axial direction (e.g., X-axis) of the endoscope connector 200. In some aspects, at least a portion of the substantially planar surface 210 may be substantially smooth (e.g., without cavities, grooves, and/or moving elements in which water or contaminants may become trapped). In an example, the entirety of the substantially planar surface 210 may be substantially smooth. Accordingly, for example, the substantial smoothness of the planar surface 210 may support improved cleanability compared to other endoscope connectors. In an example aspect, a distance between the planar surface 210 and the distal end of the endoscope connector 200 may be less than a distance between the planar surface 266 and the distal end of the endoscope connector 200 (e.g., in a direction parallel to the axial direction (e.g., X-axis) of the endoscope connector 200).

In an example in which the coupling element 220 is a non-magnetic coupling element, and the plug section 205 includes magnets 231, portions 211 of the substantially planar surface 210 (illustrated in FIG. 9B) may cover distal ends of the magnets 231 (e.g., in a direction parallel to the axial direction (e.g., X-axis) of the endoscope connector 200). For example, referring to FIG. 9B, portion 211 and portion 213 may respectively cover distal end surfaces of magnet 231 and magnet 232.

The plug section 205 may be locked in place with the endoscope adapter 400 using the coupling element 220. For example, the plug section 205 may be electrically and non-mechanically coupled (e.g., electrically and magnetically coupled) with the endoscope adapter 400. In an example, the plug section 205 (e.g., the coupling element 220) may support magnetic coupling with a coupling element 420 of the endoscope adapter 400. Example aspects of a coupling element 420 (e.g., magnets 420-$a$ and 420-$b$, a ferromagnetic material) of the endoscope adapter 400 are described with reference to FIGS. 5A, 5B, 7B, and 9B.

Accordingly, for example, coupling element 220 of the endoscope connector 200 and the coupling element 420 of the endoscope adapter 400 may be referred to as a magnetic assembly retainment feature. For example, the coupling element 220 and the coupling element 420 may support the interconnection of the endoscope connector 200 and the endoscope adapter 400, without a locking ring, grooves, or any other mechanical feature.

Additionally, or alternatively, aspects of the present disclosure support enabling and/or disabling a magnetic force at the coupling element 220 and/or at the coupling element 420 (e.g., using electromagnets described herein). In some aspects, enabling the magnetic force may provide for improvements to locking the endoscope connector 200 with the endoscope adapter 400, and disabling the magnetic force may provide for improvements to removing the endoscope connector 200 from the endoscope adapter 400.

The endoscope connector 200 may include a bushing 216 (also referred to herein as second portion of the endoscope connector 200). In an example, the bushing 216 may be circular shaped (e.g., with respect to the axial direction of the endoscope connector 200). Optionally or alternatively, the bushing 216 may be polygonal shaped. Optionally or alternatively, the bushing 216 may be squircular shaped (e.g., be formed of a combination of a circular shape and a square shape). Optionally or alternatively, the bushing 216 may be cylindrically shaped. In some aspects, the bushing 216 may include any combination of shapes (e.g., circular, polygonal, squircular, cylindrical).

In some aspects, a center of the bushing 216 and a center of the plug section 205 may be aligned with a center axis of the endoscope connector 200 in the axial direction of the endoscope connector 200. A surface 222 of the bushing 216 may have a height (having a value h4) with respect to the axial direction of the endoscope connector 200. In some aspects, the height (e.g., h4) of the surface 222 of the bushing 216 may be different from or equal to the height of any of the planar surface 270, planar surface 272, planar surface 274 (e.g., h1, h2, and/or h3). The bushing 216 may include a substantially planar surface 222 parallel to the axial direction the endoscope connector 200. For example, one or more portions of the substantially planar surface 222 may extend in the axial direction (e.g., X-axis) of the endoscope connector 200 and in a direction (e.g., Y-axis, Z-axis) perpendicular to the axial direction (e.g., X-axis) of the endoscope connector 200.

The plug section 205 may include a substantially planar surface 217 (also referred to herein as an interfacing surface) perpendicular to the axial direction the endoscope connector 200. For example, the substantially planar surface 217 may extend in directions (e.g., Y-axis and Z-axis) perpendicular to the axial direction (e.g., X-axis) of the endoscope connector 200. In some aspects, a diameter of the substantially planar surface 217 may be smaller than a diameter of the bushing 216. In some aspects, the planar surface 217 may be housed in (surrounded by and fixed in place by) the bushing 216. For example, the substantially planar surface 222 of the bushing 216 may at least partially overlap (e.g., perpendicular and/or parallel to the axial direction of the endoscope connector 200) the planar surface 217. In some aspects, at least a portion of the substantially planar surface 217 may be substantially smooth (e.g., without cavities, grooves, and/or moving elements in which water or contaminants may become trapped).

The endoscope connector 200 may include electroconductive contacts 218. In an example, each of the electroconductive contacts 218 may include a substantially planar surface that is aligned (in the axial direction (e.g., X-axis) of the endoscope connector 200) with the substantially planar surface 217. Optionally or alternatively, each of the electroconductive contacts 218 may at least partially protrude through the second substantially planar surface 217 (in the axial direction (e.g., X-axis) of the endoscope connector 200). Accordingly, for example, the electroconductive contacts 218 are located on a front face (e.g., a distal end face) of the endoscope connector 200. In some aspects, the electroconductive contacts 218 may be referred to as axial face contacts.

In some aspects, the electroconductive contacts 218 are of a same shape. For example, the electroconductive contacts 218 may be circular shaped (e.g., as illustrate at FIGS. 2A and 2B), polygonal shaped, squircular shaped (e.g., as illustrated at FIG. 11A), etc. In some aspects, centers of the electroconductive contacts 218 are spaced apart from one another according to a fixed distance (in a direction (e.g., Y-axis, Z-axis) perpendicular to the axial direction (e.g., X-axis) of the endoscope connector 200).

Figure 3A:
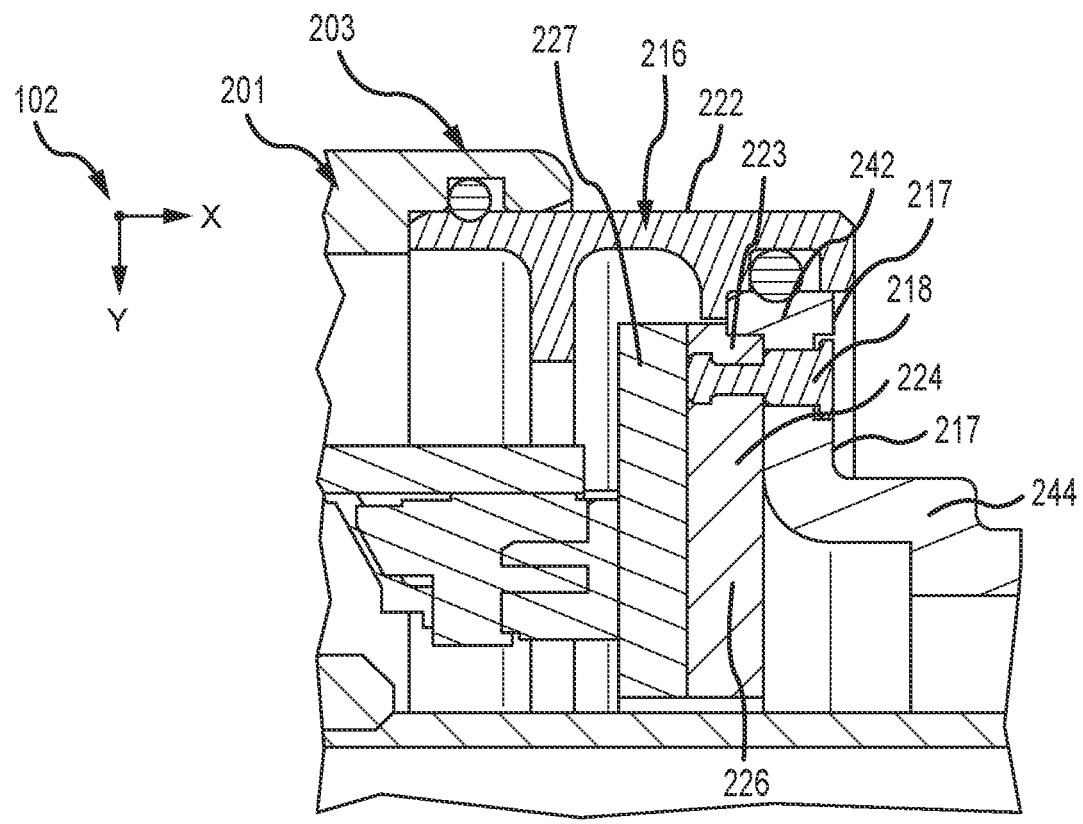
FIGS. 3A and 3B are cross-sectional diagrams illustrating example configurations of an endoscope connector in accordance with example aspects of the present disclosure.
Figure 3B:
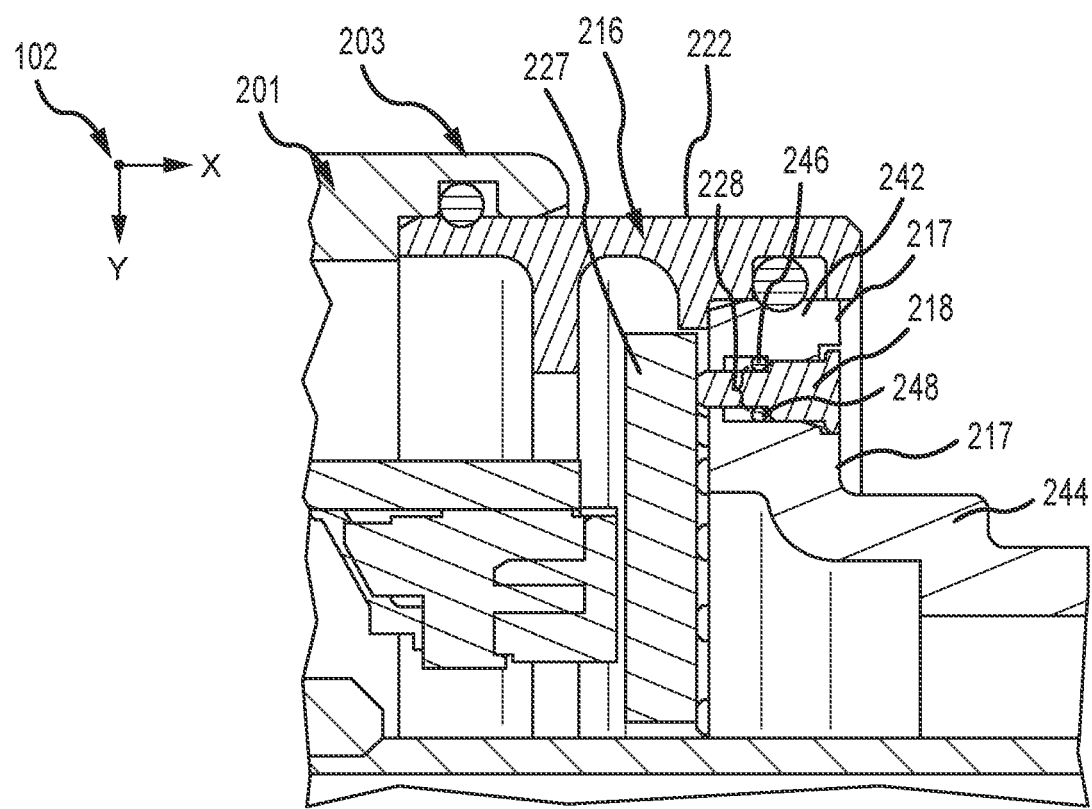

In some aspects, at least a portion of each electroconductive contact 218 is sealed in the bushing 216 using a sealing element. For example, the electroconductive contacts 218 are located on a separate substrate and are sealed using the sealing element. In some examples, the sealing element may be an O-ring seal 225, an adhesive material (e.g., an epoxy adhesive), a ceramic material, a glass material, a rubber material, a urethane material, or the like, and is not limited thereto. Examples of the sealing element are illustrated at FIGS. 3A and 3B.

In some aspects, the electroconductive contacts 218 are axially aligned with respect to the axial direction of the endoscope connector 200 (e.g., according to a placement geometry of the electroconductive contacts 218 of the endoscope connector 200). In some aspects, the electroconductive contacts 218 engage with electroconductive pins 418 (e.g., pogo pins) of the endoscope adapter 400, aspects of which are described herein. For example, the electroconductive contacts 218 and the electroconductive pins 418 may support the transmission of video signals between an endoscope (via the endoscope connector 200) and an external apparatus 300 (e.g., via the endoscope adapter 400). Example aspects of the electroconductive contacts 218 and the electroconductive pins 418 for signal transmission may support the communication of data signals (e.g., video signals) and power between an endoscope and an external apparatus 300 (e.g., a video processor, a CCU), eliminating the use of a separate cable for communication of the data signals. In an example, the electroconductive contacts 218 and the electroconductive pins 418 form a mated pair supportive of transferring endoscope power, video data, meta/identification data and control signals.

The endoscope connector 200 may include a light port 212 (also referred to herein as a light guide, connectable to a light source of an external apparatus 300) and a fluid port 214 (also referred to herein as a gas port or an insufflation port). The light port 212 and the fluid port 214 may extend in a direction parallel to the axial direction (e.g., X-axis) of the endoscope connector 200. In an example, the light port 212 and the fluid port 214 may protrude through the substantially planar surface 210 in a direction away from the proximal end of the endoscope connector 200. In some aspects, the light port 212 and the fluid port 214 may protrude from respective openings (also referred to herein as opening parts) of the substantially planar surface 210.

In some aspects, at least one dimension of the light port 212 may be larger than a corresponding dimension of the fluid port 214. For example, a diameter of the light port 212 (perpendicular to the axial direction (e.g., X-axis) of the endoscope connector 200) may be greater than a diameter of the fluid port 214. In another example, the length (in the axial direction (e.g., X-axis) of the endoscope connector 200) of a protruding portion of the light port 212 may be greater than the length of a protruding portion of the fluid port 214.

According to example aspects of the present disclosure, the planar surface 260, planar surface 262, and planar surface 264 (and the planar surface 266) are alignable with corresponding planar surface 460, planar surface 462, and planar surface 464 (and planar surface 466) of the endoscope adapter 400 such that the electroconductive contacts 218 are axially aligned with the electroconductive pins 418 of the endoscope adapter 400. Planar surface 460, planar surface 462, and planar surface 464 may be substantially planar. Surface 460, planar surface 462, and planar surface 464 may be referred to as substantially planar surfaces.

In some aspects, the planar surface 260, planar surface 262, planar surface 264 (and the planar surface 266) are alignable with the corresponding planar surface 460, planar surface 462, and planar surface 464 (and planar surface 466) of the endoscope adapter 400 such that the light port 212 and the fluid port 214 are axially aligned with an insertion port 412 and an insertion port 414 of the endoscope adapter 400. Example aspects of the planar surface 460, planar surface 462, planar surface 464, insertion port 412, and insertion port 414 are illustrated at FIGS. 4, 5A, and 5B.

In some aspects, the connector case 201 may include multiple substantially planar surfaces 203 adjacent the bushing 216. The planar surfaces 203 may be located closer to the proximal end of the endoscope connector 200 compared to the bushing 216. In an example, referring to FIGS. 2A and 2B, a planar surface 203 and another planar surface 203 of the connector case 201 may be parallel (in the axial direction (e.g., X-axis) of the endoscope connector 200) to the planar surface 260. According to example aspects of the present disclosure, based on relative positions of the ports (e.g., port 250, port 252, port 254) and the planar surfaces 203 with respect to the planar surface 260, planar surface 262, planar surface 264, light port 212, and fluid port 214, a user may identify an alignment of the planar surface 260, planar surface 262, planar surface 264, light port 212, and fluid port 214 of the endoscope connector 200 with respect to planar surface 460, planar surface 462, planar surface 464, insertion port 412, and insertion port 414 of the endoscope adapter 400.

FIGS. 3A and 3B are cross-sectional diagrams illustrating example configurations of the endoscope connector 200 in accordance with example aspects of the present disclosure.

For example, FIGS. 3A and 3B illustrate examples of sealing elements (e.g., adhesive seal 226, O-ring seal 225) used for sealing at least a portion of each electroconductive contact 218 in the bushing 216. The electroconductive contacts 218 are located on a separate substrate 227 and are sealed using the sealing element.

Referring to FIG. 3A, the adhesive seal 226 (e.g., an epoxy seal) includes a top portion 223 and a bottom portion 224.

Referring to FIG. 3B, a top portion 246 and bottom portion 248 of the O-ring seal 225 (also referred to herein as a sealing ring) are illustrated. The O-ring seal 225 may be made of rubber or a similarly suitable resilient material. In some aspects, the O-ring seal 225 may be circular or oval shaped, and the O-ring seal 225 may have a cross-sectional inner diameter (perpendicular to the axial direction (e.g., X-axis) of the endoscope connector 200) slightly exceeding an inner diameter 228 of the electroconductive contact 218. Optionally or alternatively, the O-ring seal 225 may have a cross-sectional inner diameter (perpendicular to the axial direction of the endoscope connector 200) slightly less than the inner diameter 228 of the electroconductive contact 218, such that the O-ring seal 225 is normally slightly extended or stretched when installed around the electroconductive contact 218. In some other aspects, the cross-sectional shape of the O-ring seal 225 may be square, polygonal, squircular, or other shape or configuration. In some aspects, portion 242 and portion 244 (which form a portion of the plug section 205) may exhibit a force (perpendicular to the axial direction of the electroconductive contact 218) on the O-ring seal 225.

Figure 4:
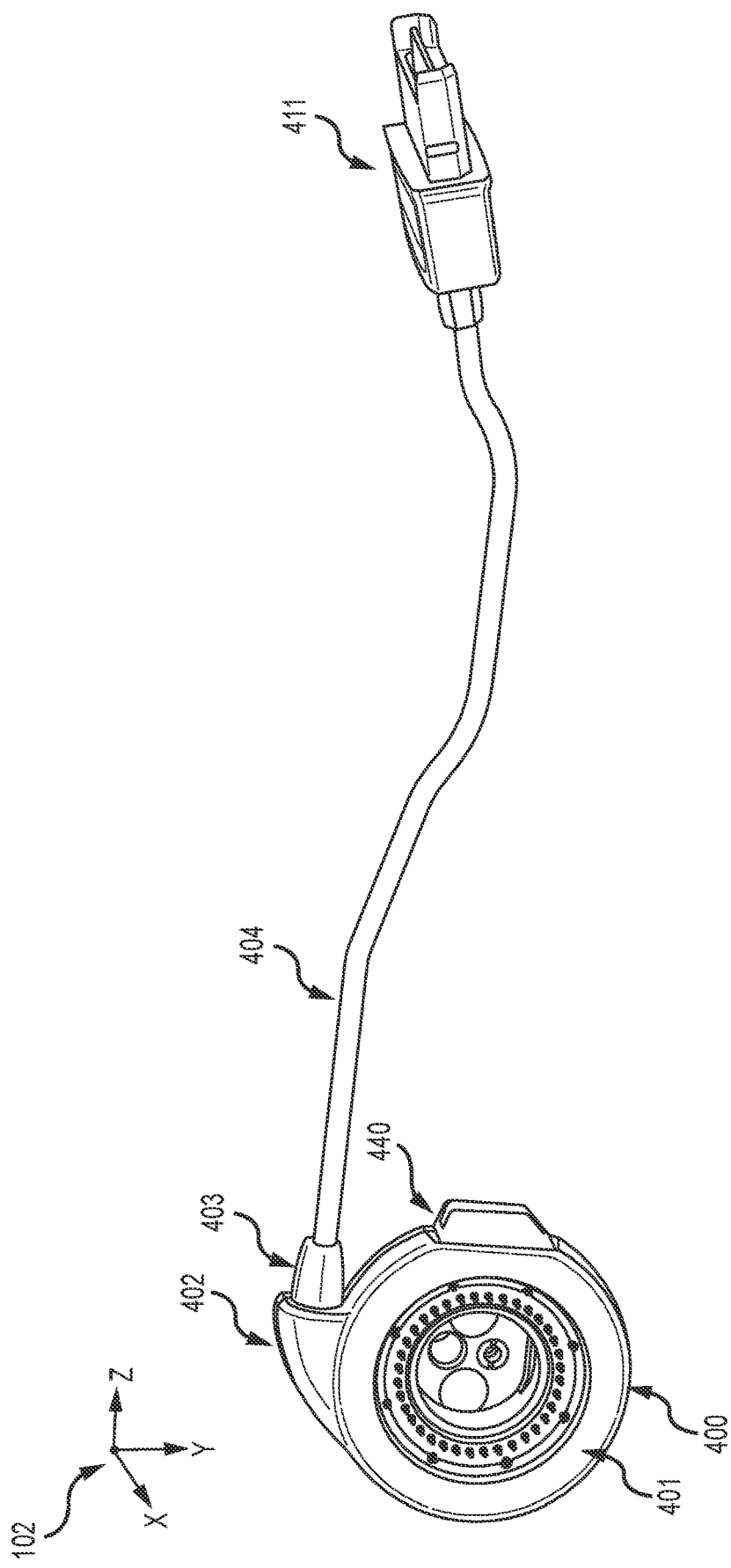
FIG. 4 is a perspective view illustrating an example of an endoscope adapter in accordance with example aspects of the present disclosure.
Figure 5A:
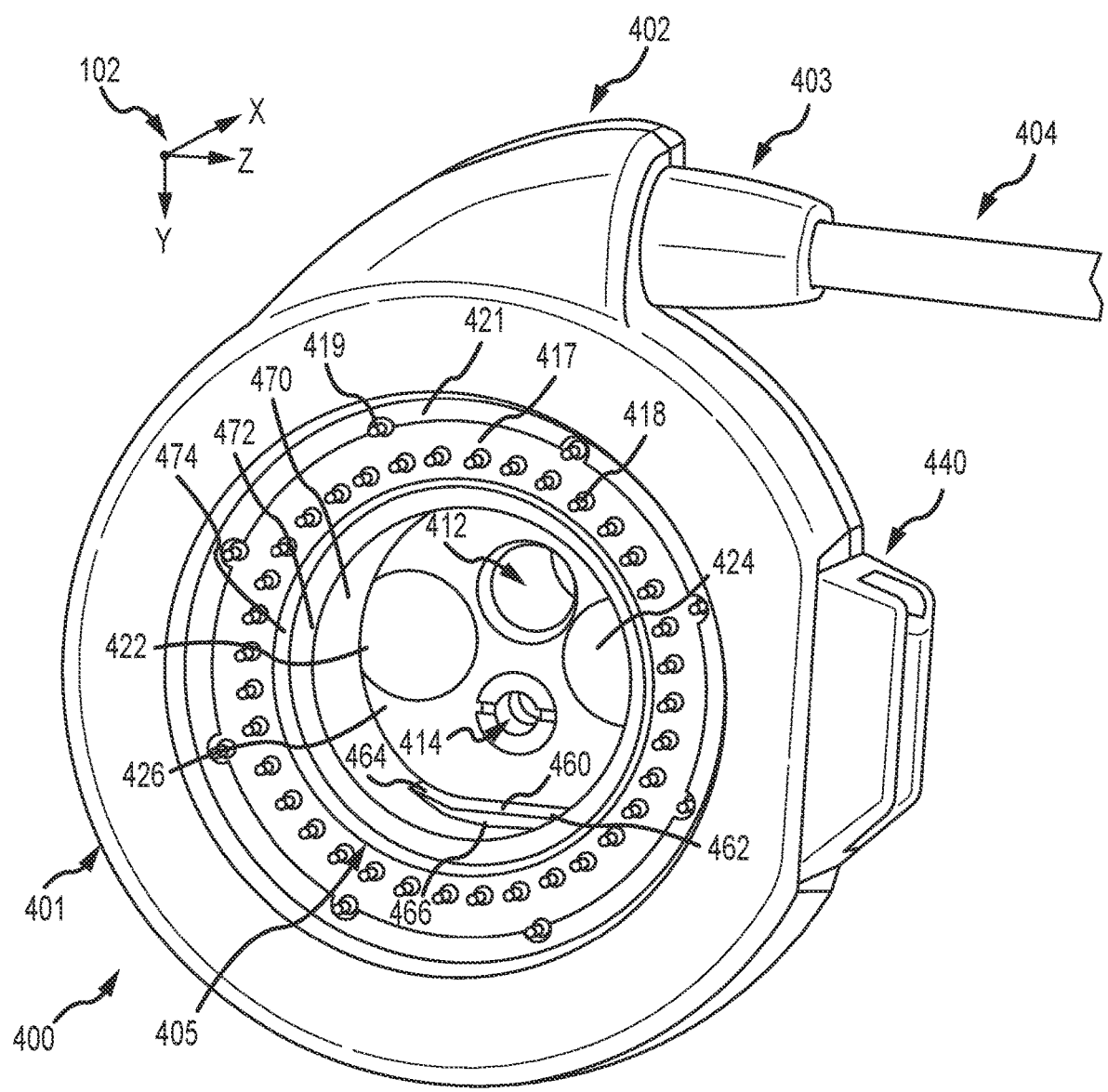
FIG. 5A is a perspective view illustrating an example of an endoscope adapter in accordance with example aspects of the present disclosure.
Figure 5B:
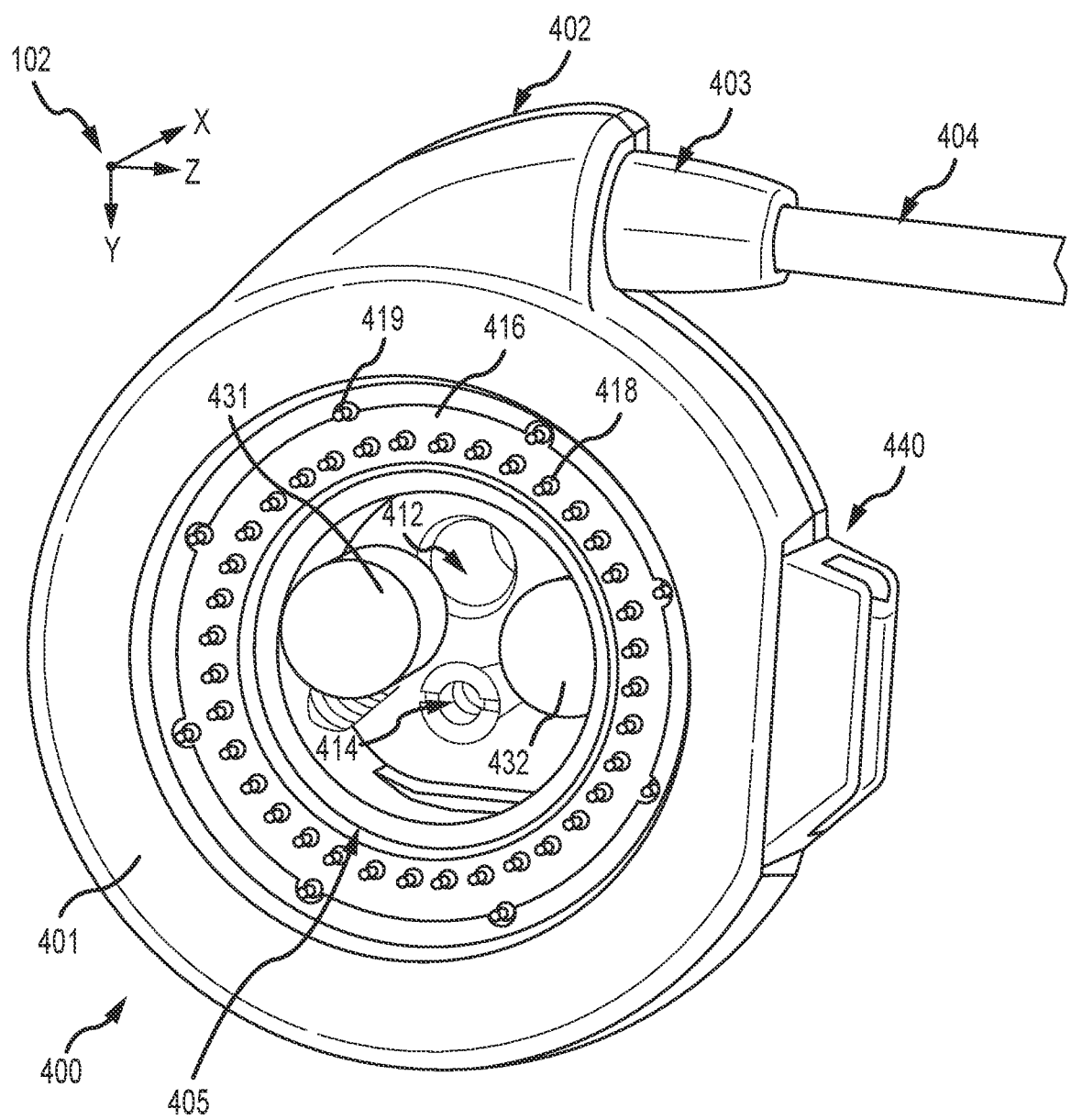
FIG. 5B is a partially-transparent perspective view of an endoscope adapter in accordance with example aspects of the present disclosure.

FIG. 4 is a perspective view illustrating an example of an endoscope adapter 400 (also referred to herein as an endoscope interface adapter) in accordance with example aspects of the present disclosure.

With reference to the coordinate system 102, an axial direction described herein of the endoscope adapter 400 corresponds with the insertion direction associated with the endoscope connector 200 (e.g., the X-axis).

According to example aspects of the present disclosure, the endoscope adapter 400 may include a receptacle portion 401, an insulator 402, a distal nut 403, a cable core 404, a proximal connector 411 (also referred to herein as a cable connector), and a plug holder 440.

The cable core 404 and the proximal connector 411 may support the communication of data signals and non-data signals (e.g., power). The insulator 402 and the distal nut 403 may be formed of materials which mitigate the flow of electric current. For example, no data signals or non-data signals are communicated through the insulator 402 or the distal nut 403.

The cable core 404 may be a relatively short (e.g., less than 200 mm in length) cable core. In an example, the cable core 404 may be permanently affixed to the receptacle portion 401 via the insulator 402. In some aspects, the length of the cable core 404 may support reduced entanglement and obstructions compared to some relatively long (e.g., 500 mm or greater in length), detachable cables. In an example, the cable 404 (e.g., cable core) spans a distance between a shroud of the endoscope adapter and the proximal connector 411. For example, the cable 404 spans a distance (e.g., 220 mm) between the distal nut 403 and the proximal connector 411.

Referring to the example of FIG. 1A, the endoscope adapter 400 may support routing of signals (e.g., data signals, non-data signals, etc.) from the endoscope adapter 400 to the video processor/CCU of the external apparatus 300 (e.g., via the cable core 404, the proximal connector 411, and a corresponding port 310 (e.g., a video port) of the external apparatus 300). For example, the proximal connector 411 may be plugged into the port 310.

Optionally or alternatively, referring to the example of FIG. 1B, the endoscope adapter 400 may support routing of signals (e.g., data signals, non-data signals, etc.) through the back of the endoscope adapter 400, through the light source of the external apparatus 300, to the video processor/CCU of the external apparatus 300. In some aspects, the example implementation may include a separate connection between light source and the CCU, and the insulator 402, the distal nut 403, the cable core 404, and the proximal connector 411 may be omitted.

Although some example views (e.g., FIG. 1B) illustrate some components (e.g., plug holder 440) of the endoscope adapter 400 while omitting some other components (e.g., insulator 402, distal nut 403, cable core 404, proximal connector 411), such example omissions are not limiting.

Optionally or alternatively, referring to the example of FIG. 1C, the cable connector 411 may be plugged into a corresponding port 312 (e.g., a video port) of the external apparatus 304 (e.g., video processor, CCU).

FIG. 5A is a perspective view illustrating an example of an endoscope adapter 400 in accordance with example aspects of the present disclosure. FIG. 5B is a partially-transparent perspective view of an endoscope adapter 400 in accordance with example aspects of the present disclosure. Example aspects of the endoscope adapter 400 are now described with reference to FIGS. 5A and 5B.

The GI adapter 400 may include features and dimensions that mirror and/or complement at least some features and dimensions of the plug section 205 of the endoscope connector 200. For example, the receptacle portion 401 and portions and/or surfaces thereof, electroconductive pins 418, electroconductive pins 419, insertion port 412, insertion port 414, etc. of the endoscope adapter 400 may mirror and/or complement the plug section 205 and portions and/or surfaces thereof, bushing 216, electroconductive contacts 218, light port 212, fluid port 414 (e.g., an air port associated with insufflation, where the fluid may be gas, water, air, etc.), etc. of the endoscope connector 200. In some aspects, some features (e.g., smoothness of a surface, materials, characteristics of a material, etc.) of the receptacle portion 401 may be the same or similar (e.g., within a threshold or tolerance) to features of the plug section 205.

Aspects of the endoscope adapter 400 are described with reference to an axial direction of the endoscope adapter 400. In some aspects, when the endoscope connector 200 and the endoscope adapter 400 are interconnected (e.g., in a connected state) according to example aspects of the present disclosure, the axial direction of the endoscope adapter 400 may be parallel to and align with the axial direction of the endoscope connector 200.

In an example, the receptacle portion 401 may include a receiving portion 405 (also referred to herein as a receiving cavity), a substantially planar surfaces 417, electroconductive pins 418, electroconductive pins 419, and a substantially planar surface 421.

The receiving portion 405 may have a shape complementary to the plug section 205. For example, the receiving portion 405 may be circular shaped, polygonal shaped, squircular shaped, cylindrical shaped, or any combination thereof.

The receiving portion 405 may include a single or multiple substantially planar surfaces 406. In some aspects, the planar surface 460, planar surface 462, and planar surface 464 (individually, or in combination) may be referred to as a planar portion. In an example, the planar portion may include a substantially planar surface (e.g., corresponding to any of planar surface 460, planar surface 462, and planar surface 464) that is parallel (e.g., extends along the Z-axis) to an axial direction (e.g., X-axis) of the endoscope adapter 400.

According to example aspects of the present disclosure, the planar surface 460, planar surface 462, and planar surface 464 (e.g., dimensions, shapes, etc. thereof) may respectively mirror the planar surface 260 through planar surface 264 of the plug section 205. In some aspects, the planar surface 460 may have a length (perpendicular to the axial direction of the endoscope adapter 400) different from a respective length (perpendicular to the axial direction of the endoscope adapter 400) of at least one of the planar surface 462 and the planar surface 464. Optionally or alternatively, the planar surface 460 may have a length equal to a respective length of at least one of the planar surface 462 and the planar surface 464. In some aspects, the planar surface 460 through the planar surface 464 may be equal in width (in the axial direction (e.g., X-axis) of the endoscope adapter 400).

The receiving portion 405 may include a substantially planar surface 466. In some aspects, the planar surface 466 may be perpendicular to the axial direction of the endoscope adapter 400. For example, the substantially planar surface 466 may extend in directions (e.g., Y-axis and Z-axis) perpendicular to the axial direction (e.g., X-axis) of the endoscope adapter 400. The planar surface 466 (e.g., dimensions, shapes, etc. thereof) may complement the planar surface 266 of the plug section 205. In some aspects, a first distance between the planar surface 422, the planar surface 424, and/or the planar surface 426 and a distal end of the endoscope adapter 400 is different from (e.g., greater than) a second distance between the planar surface 466 and the distal end.

The receiving portion 405 may include additional substantially planar surfaces (e.g., planar surface 470, planar surface 472, planar surface 474, etc.). The planar surface 470, planar surface 472, and planar surface 474 (e.g., dimensions, shapes, etc. thereof) may mirror the planar surface 270, planar surface 272, and planar surface 274 of the plug section 205. In some aspects, the planar surface 470, planar surface 472, and planar surface 474 may be parallel to the axial direction (e.g., X-axis) of the endoscope adapter 400. For example, the planar surface 470, planar surface 472, and planar surface 474 may each extend in the axial direction (e.g., X-axis) of the endoscope connector 200.

In some aspects, the planar surfaces 422 through 426, the planar surfaces 460 through 464 (e.g., forming a corresponding planar portion), the planar surface 466, and the planar surfaces 470 through 474, and may be alignable with the planar surface 210, the planar surfaces 260 through 264 (e.g., forming a corresponding planar portion), the planar surface 266, and the planar surfaces 270 through 274 such that the set of electroconductive pins 418 are axially aligned with the electroconductive contacts 218 of the endoscope connector 200.

Figure 9A:
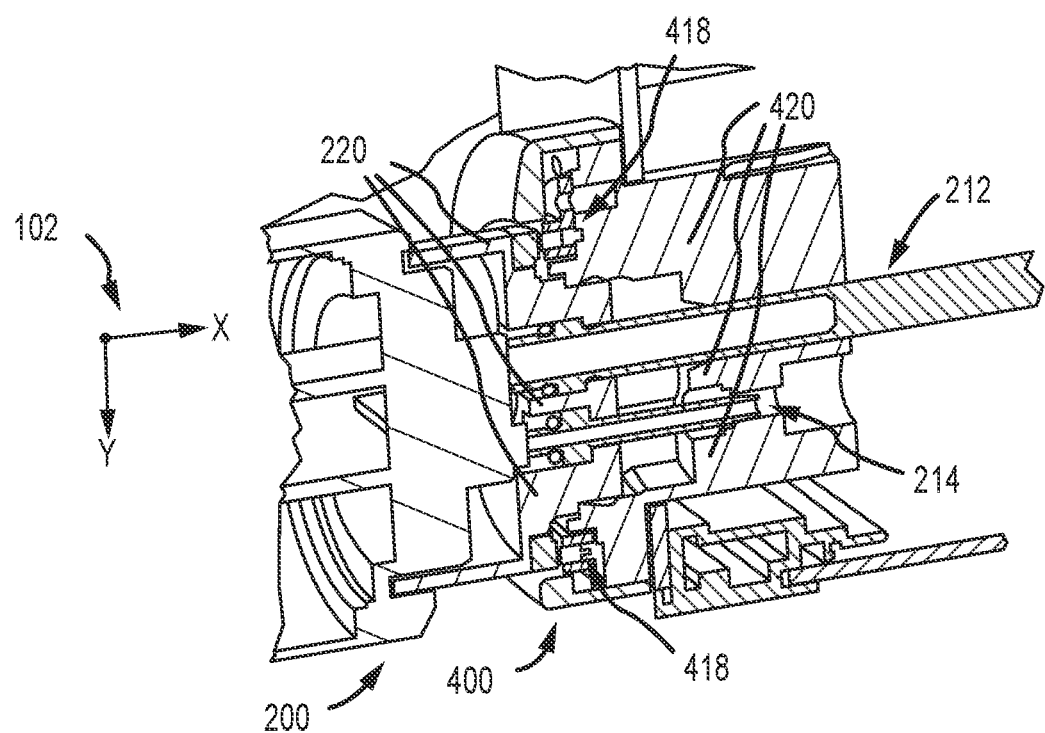
FIGS. 9A and 9B are cross-sectional diagrams illustrating examples of a connected state between an endoscope connector and an endoscope adapter in accordance with example aspects of the present disclosure.
Figure 9B:
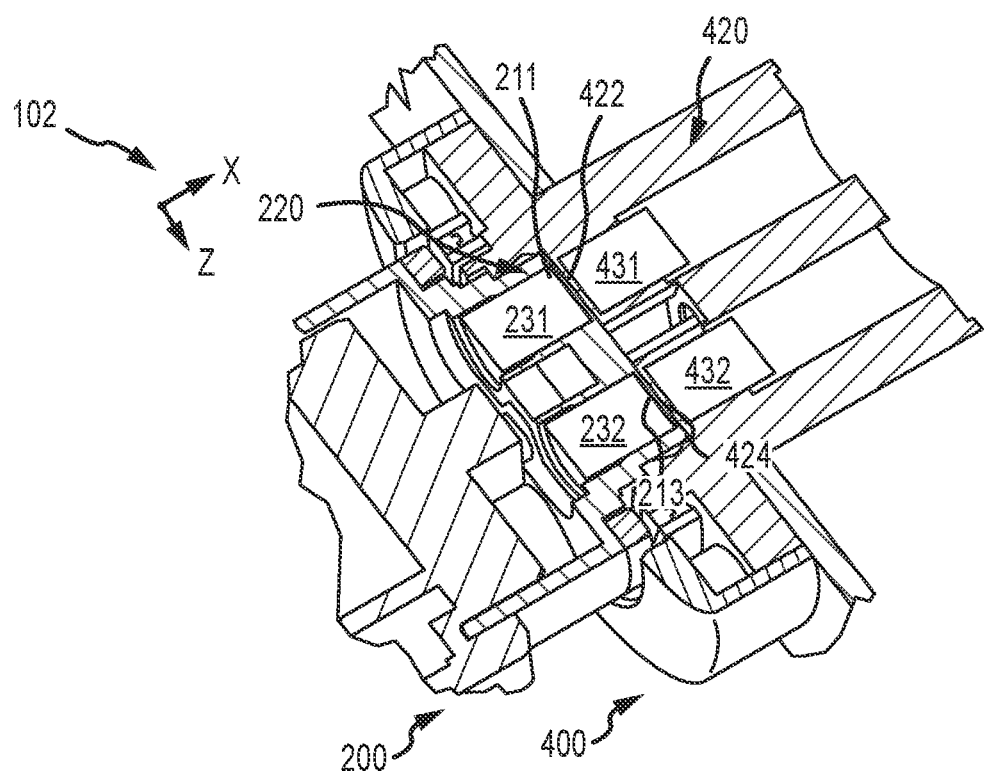

The receptacle portion 401 may include a coupling element 420 (a cross-section of which is illustrated at FIGS. 9A and 9B). The coupling element 420 (illustrated at FIGS. 9A and 9B, not visible in FIGS. 5A and 5B) may include some example aspects of the coupling element 220 of the endoscope connector 200. For example, the coupling element 420 may include one or more magnets (e.g., a magnet 431 and a magnet 432 illustrated at FIGS. 5B and 9B). In an example, the magnets 431 may be integrated within the coupling element 420 (e.g., as illustrated at FIG. 9B). In some aspects, the coupling element 420 may be integrated with or separate from (e.g., covered by) any of the planar surface 422, the planar surface 424, the planar surface 426, the planar surface 460, the planar surface 462, the planar surface 464, and the planar surface 466.

In an example aspect, the magnets 431 may be electromagnets (e.g., including a core of magnetic material such as iron) which may be magnetized in response to an electric current. In some cases, an endoscope, the endoscope connector 200, and/or an external apparatus 300 described herein may include a user interface (e.g., a switch, a button, a touch screen, etc.) for activating the electric current (e.g., for magnetizing or demagnetizing the magnets 431).

Optionally or alternatively, the magnets 431 may be permanent magnets (e.g., neodymium magnets). In some aspects, the magnets 431 may have an outer diameter (in a direction (e.g., Z-axis) perpendicular to the axial direction (e.g., X-axis) of the endoscope connector 200) of 0.375 inches and a length (in the axial direction (e.g., X-axis) of the endoscope connector 200) of 0.500 inches. Optionally or alternatively, the magnets 431 may be replaced with magnetic elements formed of a ferromagnetic material (not illustrated).

The coupling element 420 may have a substantially planar surface (e.g., planar surface 422, planar surface 424, and/or planar surface 426 illustrated in FIG. 5A) perpendicular to the axial direction (e.g., X-axis) of the endoscope adapter 400. For example, the substantially planar surface (e.g., any or all of planar surface 422, planar surface 424, planar surface 426) may extend in directions (e.g., Y-axis and Z-axis) perpendicular to the axial direction (e.g., X-axis) of the endoscope adapter 400. The substantially planar surface 422, planar surface 424, and/or planar surface 426 (e.g., dimensions, shapes, etc. thereof) may mirror at least a portion of the planar surface 210 of the plug section 205. In an example aspect, a distance between the planar surface 422, planar surface 424, and/or planar surface 426 and the distal end of the endoscope adapter 400 may be less than a distance between the planar surface 417 and the distal end of the endoscope adapter 400.

In an example in which the coupling element 420 includes magnets 431 (e.g., magnet 431 and magnet 432 illustrated in FIG. 9B), portions of a substantially planar surface (e.g., any or all of planar surface 422 and/or planar surface 424) may cover distal ends of the magnets 431 (e.g., in a direction parallel to the axial direction (e.g., X-axis) of the endoscope adapter 400). For example, referring to FIG. 9B, planar surface 422 and planar surface 424 may respectively cover distal end surfaces of magnet 431 and magnet 432.

Optionally or alternatively, the coupling element 420 may be a magnetic coupling element formed of a ferromagnetic material (e.g., corrosion resistant stainless steel), and the coupling element 420 may be implemented without magnets 431. In an example, any or all of planar surface 422, planar surface 424, and planar surface 426 may be formed of the ferromagnetic material.

The substantially planar surface 417 (also referred to herein as an interfacing surface) and the planar surface 421 may each be perpendicular to the axial direction (e.g., X-axis) of the endoscope adapter 400. For example, the substantially planar surface 417 and the planar surface 421 may each extend in directions (e.g., Y-axis and Z-axis) perpendicular to the axial direction (e.g., X-axis) of the endoscope adapter 400. In some aspects, the planar surface 417 and the planar surface 421 (e.g., dimensions, shapes, etc. thereof) may respectively correspond to (e.g., mirror in the axial direction(s) of the endoscope connector 200 and the endoscope adapter 400) the planar surface 217 and the planar surface 221 of the endoscope connector 200.

Figure 7A:
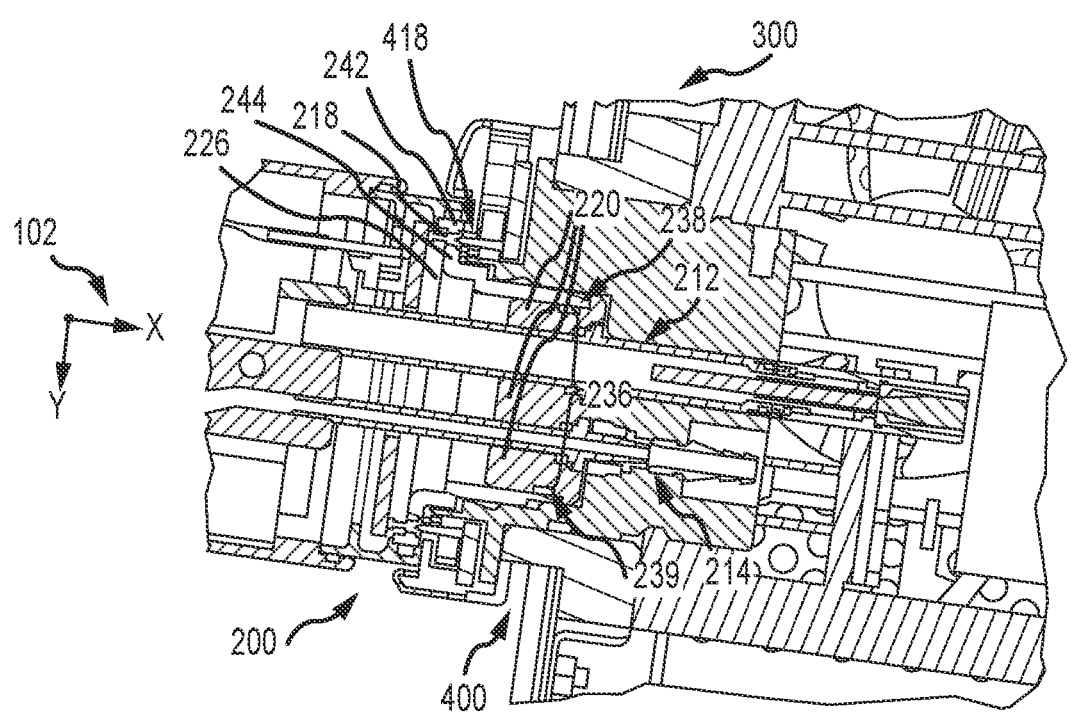
FIGS. 7A and 7B are cross-sectional diagrams illustrating examples of a connected state between an endoscope connector and an endoscope adapter in accordance with example aspects of the present disclosure.
Figure 7B:
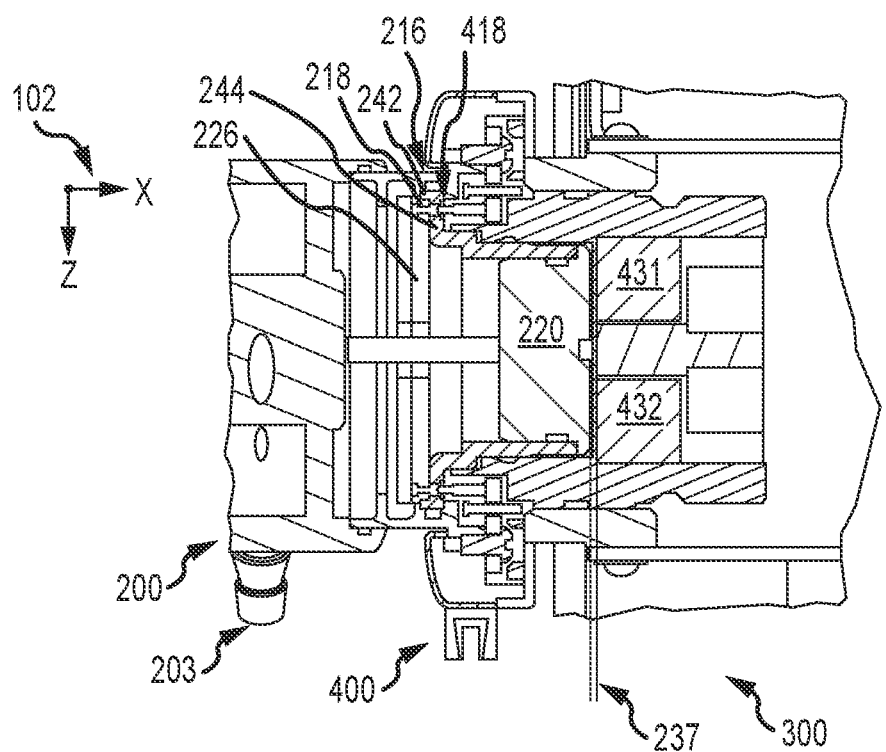

The receptacle portion 401 may include electroconductive pins 418 (also referred to herein as signal pins). The electroconductive pins 418 may be, for example, spring loaded probes (e.g., pogo pins including a plunger, a tube, and a spring) supportive of an electrical connection between the endoscope (via the electroconductive contacts 218 of the endoscope connector 200) and a printed circuit board (PCB) located in a shroud of the endoscope adapter 400. In some examples, the electroconductive pins 418 may be of the same shape or may be of different shapes. In an example, each electroconductive pin 418 may be cylinder shaped or non-cylindrically shaped (e.g., squircular shaped, polygon shaped, etc.), and each electroconductive pin 418 may include two spring-loaded pins. In an example, a surface area of a contact point (e.g., a distal end) of an electroconductive pin 418 may be equal to or less than a surface area of a corresponding electroconductive contact 218 (e.g., as illustrated at FIGS. 7A, 7B, and 8).

In some aspects, positions and/or spacing of the electroconductive pins 418 may correspond to (e.g., align with, in a direction (e.g., Y-axis, Z-axis) perpendicular to the axial direction (e.g., X-axis) of the endoscope connector 200 and GI adapter 400) positions and/or spacing of the electroconductive contacts 218 of the endoscope connector 200. In some aspects, the positions and/or spacing of the electroconductive contacts 218 and the electroconductive pins 418 may support and maintain high speed signal integrity (e.g., 4 Gbps or higher).

The receptacle portion 401 may include electroconductive pins 419. The electroconductive pins 419 may include examples of aspects of the electroconductive pins 418. Example comparative aspects (e.g., positioning, characteristics, etc.) of the electroconductive pins 418 and electroconductive pins 419 are described herein. Other aspects (e.g., shielding aspects, signal aspects, etc.) of the electroconductive pins 418 and electroconductive pins 419 are later described with reference to FIG. 8.

In some aspects, each of the electroconductive pins 418 and pins 419 may at least partially protrude through the substantially planar surface 417. Accordingly, for example, the electroconductive pins 418 (and electroconductive pins 419) are located on a front face (e.g., a distal end face) of the endoscope adapter 400. In some aspects, the electroconductive pins 418 (and electroconductive pins 419) may be referred to as axial face contacts or axial face contact pins.

In an example, the electroconductive pins 418 may be of the same length (in the axial direction (e.g., X-axis) of the endoscope adapter 400) when non-compressed (e.g., when the endoscope connector 200 and the endoscope adapter 400 are not coupled) or when compressed (e.g., when the endoscope connector 200 and the endoscope adapter 400 are coupled). In some aspects, the electroconductive pins 419 may be of the same length (in the axial direction (e.g., X-axis) of the endoscope adapter 400) when non-compressed (e.g., when the endoscope connector 200 and the endoscope adapter 400 are not coupled) or when compressed (e.g., when the endoscope connector 200 and the endoscope adapter 400 are coupled).

In some aspects, the electroconductive pins 418 are of a same shape (e.g., circular shaped, polygonal shaped, squircular shaped, cylindrical shaped, or any combination thereof). In some aspects, centers of the electroconductive pins 418 are spaced apart from one another according to a fixed distance (in a direction (e.g., Y-axis, Z-axis) perpendicular to the axial direction (e.g., X-axis) of the endoscope adapter 400). In some aspects, the electroconductive pins 418 are axially aligned with respect to the axial direction of the endoscope adapter 400 (e.g., according to a placement geometry of the electroconductive pins 418). For example, the electroconductive pins 418 may be positioned according to a shape (e.g., a circle) having a dimension (e.g., a diameter) perpendicular to the axial direction (e.g., X-axis) of the endoscope adapter 400. In some aspects, the electroconductive pins 418 may extend in a direction (e.g., Y-axis, Z-axis) parallel to the axial direction (e.g., X-axis) of the endoscope adapter 400.

In some aspects, the electroconductive pins 419 are of a same shape (e.g., circular shaped, polygonal shaped, squircular shaped, cylindrical shaped, or any combination thereof). In some aspects, centers of the electroconductive pins 419 are spaced apart from one another according to a fixed distance (in a direction (e.g., Y-axis, Z-axis) perpendicular to the axial direction (e.g., X-axis) of the endoscope adapter 400). In some aspects, the electroconductive pins 419 are axially aligned with respect to the axial direction (e.g., X-axis) of the endoscope adapter 400 (e.g., according to a placement geometry of the electroconductive pins 419). For example, the electroconductive pins 419 may be positioned according to a shape (e.g., a circle) having a dimension (e.g., a diameter) perpendicular to the axial direction (e.g., X-axis) of the endoscope adapter 400. In some aspects, the electroconductive pins 418 may extend in a direction parallel to the axial direction (e.g., X-axis) of the endoscope adapter 400.

In some cases, the electroconductive pins 418 and the electroconductive pins 419 may be of the same shape. Optionally or alternatively, the electroconductive pins 418 may be differently shaped compared to the electroconductive pins 419.

In an example, a first distance between at least one electroconductive pin 418 of the set of electroconductive pins 418 and a central axis of the endoscope adapter is different from (e.g., less than) a second distance between at least one second electroconductive pin 419 of the set of second electroconductive pins 419 and the central axis of the endoscope adapter. For example, the electroconductive pins 418 may be positioned according to a circle having a first diameter perpendicular to the axial direction (e.g., X-axis) of the endoscope adapter 400, and the electroconductive pins 419 may be positioned according to a circle having a second diameter perpendicular to the axial direction (e.g., X-axis) of the endoscope adapter 400. In an example, the first diameter may be smaller than the second diameter.

The insertion port 412 may have a diameter (perpendicular to the axial direction of the endoscope adapter 400) that complements (e.g., is larger than) a diameter of the light port 212 of the endoscope connector 200. In some aspects, a light source (not shown) of the external apparatus 300 may be accessible via the insertion port 412. The insertion port 414 may have a diameter (perpendicular to the axial direction (e.g., X-axis) of the endoscope adapter 400) that complements (e.g., is larger than) a diameter of the fluid port 214 of the endoscope connector 200. In some aspects, a fluid source (not shown) of the external apparatus 300 may be accessible via the insertion port 414. The light port 212 and the fluid port 214 of the endoscope connector 200 may be insertable into and removable from the insertion port 412 and the insertion port 414, respectively.

The insertion port 412 (and the light port 212) may communicate (e.g., transfer) light emitted by a light source of an external apparatus 300 to an endoscope. The insertion port 412 (and the fluid port 212) may communicate (e.g., transfer) fluid output by a fluid source of an external apparatus 300 to an endoscope.

In some aspects, a center of the receiving portion 405 and/or a center of a shape of the planar surface 417 may be aligned with a center axis of the endoscope adapter 400 in the axial direction of the endoscope adapter 400.

According to example aspects of the present disclosure, the endoscope adapter 400 (also referred to herein as an interface adapter) may support relatively quick, low-force, electro-mechanical coupling of endoscopes (e.g., via endoscope connector 200) to light sources and CCUs for combined light, power, and data transmission. For example, the endoscope adapter 400 (e.g., in combination with the endoscope connector 200) may support an insertion force of less than 0 pounds of force (also referred to herein as pound-force (lbf)), or zero-force insertion. In some aspects, the endoscope adapter 400 (e.g., in combination with the endoscope connector 200) may support a retraction force of between 10 lbf to 12 lbf. In some aspects, the insertion force and the retraction force may be parallel to the axial direction (e.g., X-axis) of the endoscope connector 200 and/or the axial direction (e.g., X-axis) of the endoscope adapter 400.

Aspects of the present disclosure as described herein support a spring force (e.g., created by the electroconductive pins 418) and positive attraction forces (e.g., between the coupling element 220 and the coupling element 420) that may yield a low or zero insertion-force connection. For example, the magnitude of the spring force and the magnitude of the positive attraction forces may be equal to (i.e., offset) one another.

In some cases, the insertion force and retraction force may be based on the example implementations of the coupling element 220 and the coupling element 420 described herein. For example, the insertion force and retraction force may be based on magnet size implemented at coupling element 220 and/or coupling element 420. In another example, the insertion force and retraction force may be based on magnet type (e.g., permanent, electromagnetic, etc.) implemented at coupling element 220 and/or coupling element 420. In some other aspects, the insertion force and retraction force may be based on a distance (e.g., an air gap 237 illustrated at FIG. 7B) implemented between coupling element 220 and coupling element 420 when the endoscope connector 200 and GI adapter 400 are magnetically coupled (e.g., when the endoscope connector 200 is fully inserted into the endoscope adapter 400).

Accordingly, for example, aspects of the present disclosure support optimization and configuration of the retraction force through magnetic material selection, geometry (e.g., location, positions, size, shape) of the coupling element 220, and geometry of the coupling element 420. In some aspects, the coupling element 420 (e.g., magnets 420-a and 420-b) and coupling element 220 may replace high-insertion force spring clip/gland retention mechanisms implemented in some other GI adapters and endoscope connectors.

Aspects of the endoscope adapter 400 described herein support a single interconnection mechanism between an endoscope (e.g., via the endoscope connector 200) and the endoscope adapter 400, in which the interconnection mechanism integrates power and signal transmission functionality of a detachable cable with the retention/positioning functionality of an endoscope adapter. The GI adapter 400 supports electrical connection for power and signal transmission through axially-aligned electrical contacts on the interfacing surfaces of the endoscope adapter 400 and endoscope connector 200. For example, the endoscope adapter 400 and endoscope connector 200 may support ground connections electroconductive pins 419, while supporting data signal (e.g., video signal, control signal, etc.) transmission through electroconductive contacts 218 and electroconductive pins 418. Optionally or alternatively, a first subset of the electroconductive contacts 218 and a first subset of the electroconductive pins 418 may support power transmission and/or ground connections, and a second subset of the electroconductive contacts 218 and a second subset of the electroconductive pins 418 may support data transmission. In some aspects, the endoscope adapter 400 and the endoscope connector 200 may support energy efficient power transmission via the electroconductive contacts 218 and the electroconductive pins 418, without moving parts (and accordingly, for example, no mechanical wear).

Aspects of the endoscope adapter 400 and endoscope connector 200 support single-step connection, which may eliminate the use of a separate cable for communication of power and/or data signals. In conjunction, such features may support single-step electro-mechanical coupling of an endoscope (via the endoscope connector 200) to the light source and CCU (at an external apparatus 300 or multiple external apparatuses 300). Accordingly, for example, aspects of the single-step connection supported by the endoscope adapter 400 and endoscope connector 200 may eliminate the two steps implemented in other endoscopy systems for connecting the distal end of an endoscope connector to an endoscope plug and for connecting the proximal end of the endoscope connector to a CCU, respectively.

Further, in some aspects, the endoscope adapter 400 may include a groove feature (e.g., corresponding to planar surface 472) which may support backwards mechanical compatibility with some gastroscopes.

As described herein, aspects of the endoscope adapter 400 differ from those of other GI adapters which use spring-loaded electrical contacts that are aligned radially (i.e., positioned on a surface that is parallel to an insertion direction of a corresponding endoscope and endoscope plug) and pin/socket electrical contacts that are aligned axially (i.e., positioned on a surface/plane that is perpendicular to the insertion direction of the endoscope and endoscope plug). In some cases, spring-loaded contacts that are aligned radially are subjected to increased wear and risk of damage, since the insertion of the endoscope plug is perpendicular to the compression direction of the contact. In some other cases, pin/socket electrical contacts aligned axially may have relatively high insertion forces and are susceptible to dust and debris buildup that could prevent reliable electrical connection.

Aspects of the endoscope adapter 400 provide advantages over other GI adapters which provide a mechanical interface (e.g., retention and positioning of an endoscope plug relative to a light source) but are incapable of providing power or signal transmission. Accordingly, for example, aspects of the present disclosure support a reduced number of steps, a reduced number of cables, and reduced cable entanglement associated with interconnecting an endoscope and external apparatuses (e.g., CCUs, light sources), providing improved user convenience (e.g., improved visibility of and access to equipment controls, displays, etc.).

Aspects of the endoscope connector 200 and GI adapter 400 may provide advantages of some techniques for retaining endoscope plugs. For example, according to some techniques, an endoscope plug is retained by a spring clip (gland retention mechanism) that is compressed during insertion of the endoscope plug and subsequently expands into a groove in an endoscope adapter. Such retention mechanisms experience high levels of wear throughout the lifetime thereof, resulting in significant increases in insertion and/or retraction forces for the user over time and with increased usage. In some cases, to achieve repeatable, consistent insertion and/or retention forces for such retention mechanisms, strict (e.g., within a threshold) manufacturing tolerances are required for the clip and mating gland features. However, adherence to such manufacturing tolerances may result in relatively high insertion forces associated with connecting an endoscope plug to an endoscope adapter and light source, preventing proper connection from being established.

Aspects of the endoscope connector 200 and GI adapter 400 provide benefits associated with overhead (e.g., cost and development time) compared to other implementations of traditional pin-to-pad electrical contacts. In some cases, aspects of the present disclosure provide advantages over data communication mechanisms incorporating fiber optics, as incorporating fiber optic communications into an endoscope would incur considerable cost and development overhead associated with endoscope redesign. Further, for example, materials (e.g., a glass or plastic core) associated with fabricating fiber optic cables may be relatively less durable compared to using electroconductive contacts 218 and electroconductive pins 418 as described herein.

Further, aspects of the present disclosure described herein provide advantages over other techniques for power transmission. For example, electromagnetic power transmission (i.e. inductive coupling) may support wireless delivery of power (and low speed data communication), but may present electromagnetic compatibility (e.g., inductive coupling) challenges with high susceptibility to electromagnetic interference (EMI) and radiated emissions. For example, using inductive coupling on an endoscope in an operating room could present problematic interactions with implantable medical devices that also use inductive coupling, such as pacemakers.

Figure 6:
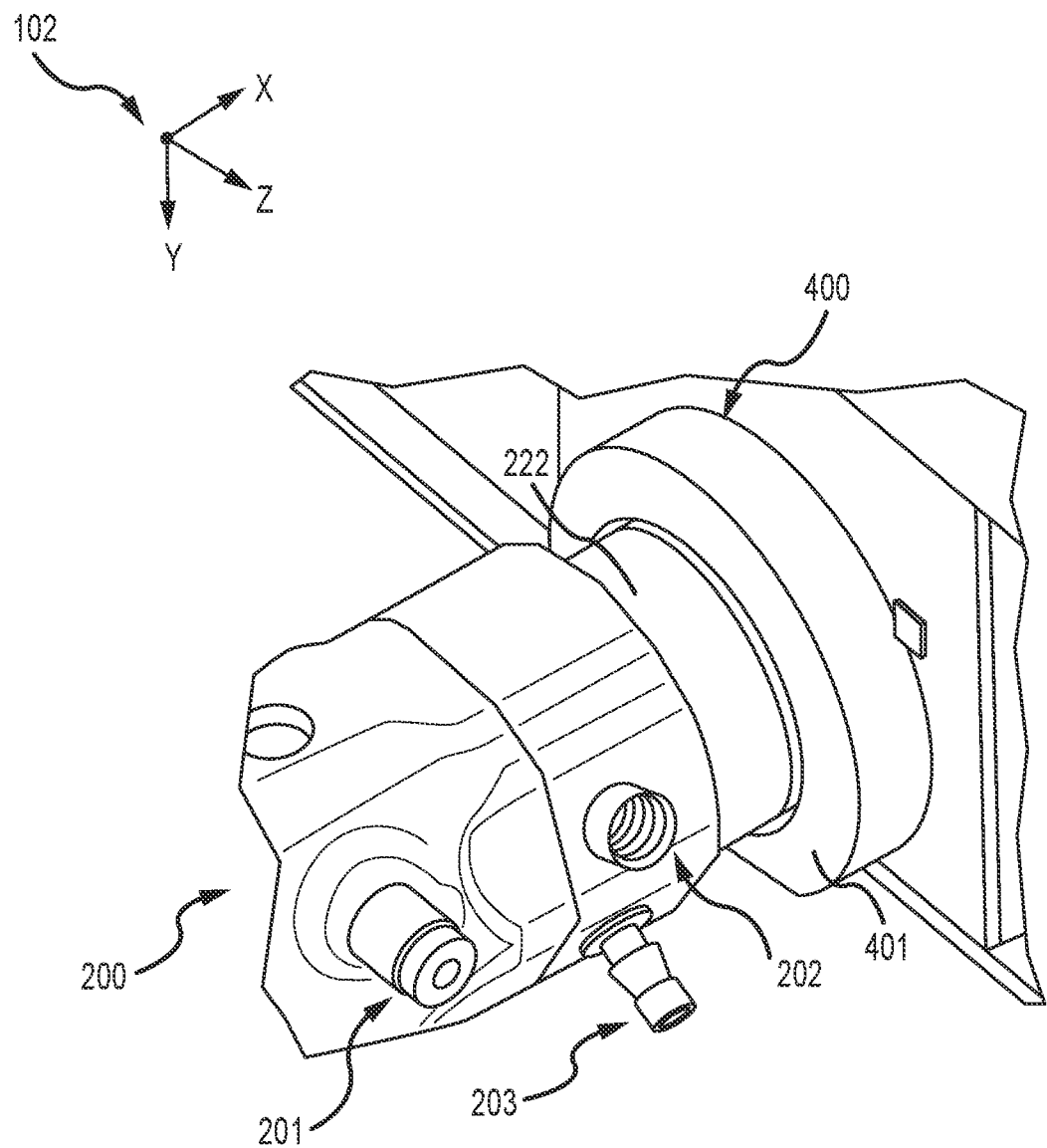
FIG. 6 is a perspective view illustrating an example of a connected state between an endoscope connector connected to an endoscope adapter in accordance with example aspects of the present disclosure.

FIG. 6 is a perspective view illustrating an example of a connected state between an endoscope connector 200 connected to an endoscope adapter 400 in accordance with example aspects of the present disclosure. For example, as illustrated in FIG. 6, the endoscope connector 200 is in an electrically and non-mechanically (e.g., magnetically) coupled state with the endoscope adapter 400 such that that plug section 205 (not visible) is completely inserted into the receiving portion 405 (not visible).

FIGS. 7A and 7B are cross-sectional diagrams illustrating examples of a connected state between an endoscope connector 200 and an endoscope adapter 400 in accordance with example aspects of the present disclosure.

Referring to the example of FIG. 7A, aspects of an O-ring seal 235 (also referred to herein as a sealing ring) for sealing the coupling element 220 are described herein. In some aspects, the O-ring 235 may include example aspects of O-ring 225. A top portion 238 and bottom portion 239 of the O-ring seal 235 are illustrated in FIG. 7A.

In an example, the O-ring seal 235 may be circular or oval shaped, and the O-ring seal 235 may have a cross-sectional inner diameter (perpendicular to the axial direction (e.g., X-axis) of the endoscope connector 200) slightly exceeding an inner diameter 236 of the coupling element 220. Optionally or alternatively, the O-ring seal 235 may have a cross-sectional inner diameter (perpendicular to the axial direction (e.g., X-axis) of the endoscope connector 200) slightly less than the inner diameter 236, such that the O-ring seal 235 is normally slightly extended or stretched when installed around the coupling element 220.

Referring to the example of FIG. 7B, according to example aspects of the present disclosure, coupling element 220 may be a magnetic coupling element (e.g., a ferromagnetic material, a permanent magnet, an electromagnet, etc.), and magnets 431 may be permanent magnets or electromagnets. Optionally or alternatively, magnets 431 may be omitted as described herein. For example, planar surface 422, planar surface 424, and/or planar surface 426 (illustrated in FIG. 5A) of the endoscope adapter 400 may be magnetic (e.g., formed of a ferromagnetic material), and magnets 431 may be omitted.

Referring to FIG. 7B, an example air gap 237 is illustrated, on which the insertion force and retraction force described herein may be based. For example, the insertion force and retraction force associated with magnetically coupling and decoupling the endoscope connector 200 and GI adapter 400 may be based on a distance corresponding to the air gap 237. In an example, the distance corresponding to the air gap 237 is a distance between the planar surface 210 of the endoscope connector 200 and the planar surface 422, planar surface 424, and/or planar surface 426 of the endoscope adapter 400.

Figure 8A:
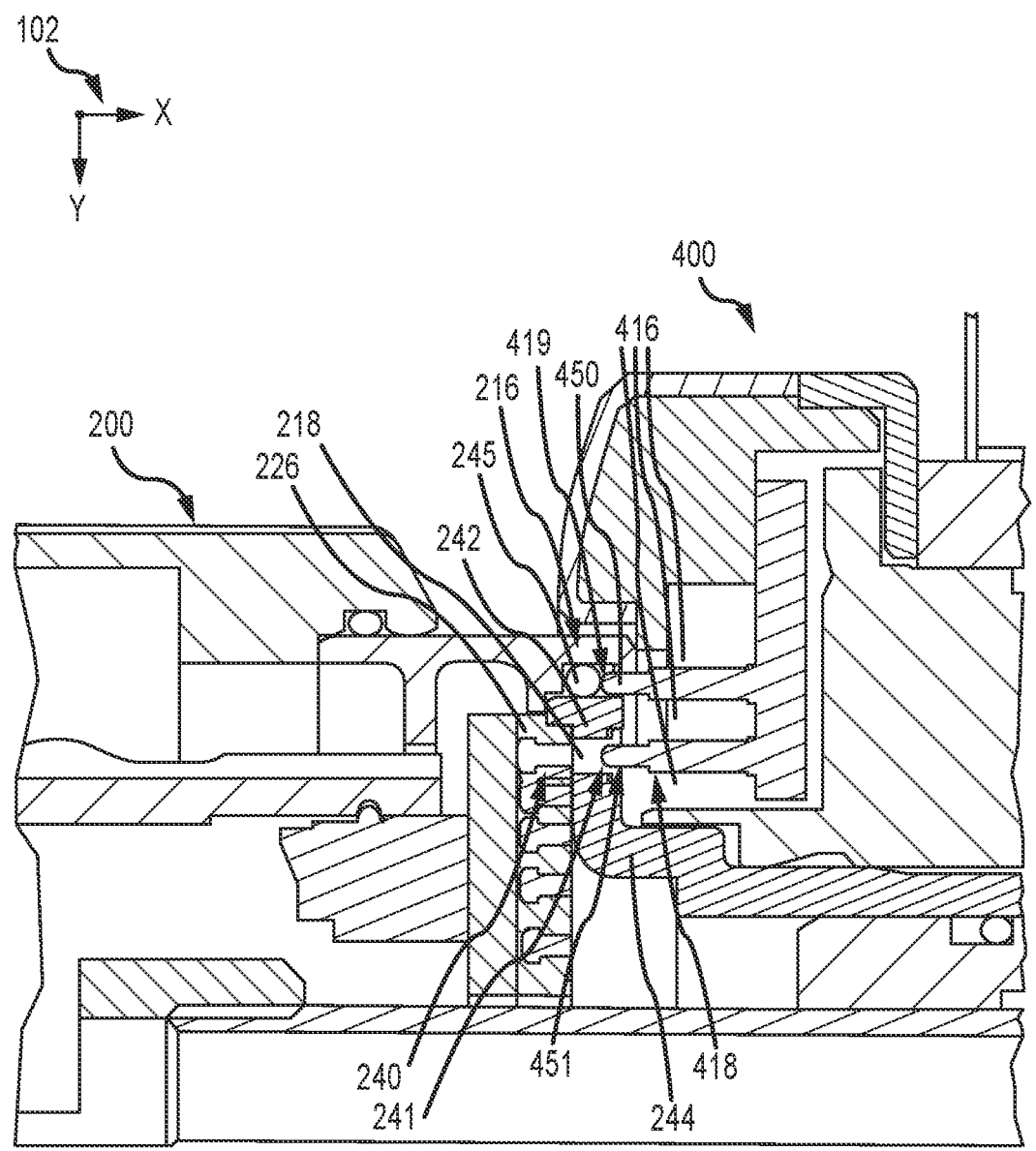
FIG. 8A is a cross-sectional diagram illustrating an example of a connected state between an endoscope connector and an endoscope adapter in accordance with example aspects of the present disclosure.
Figure 8B:
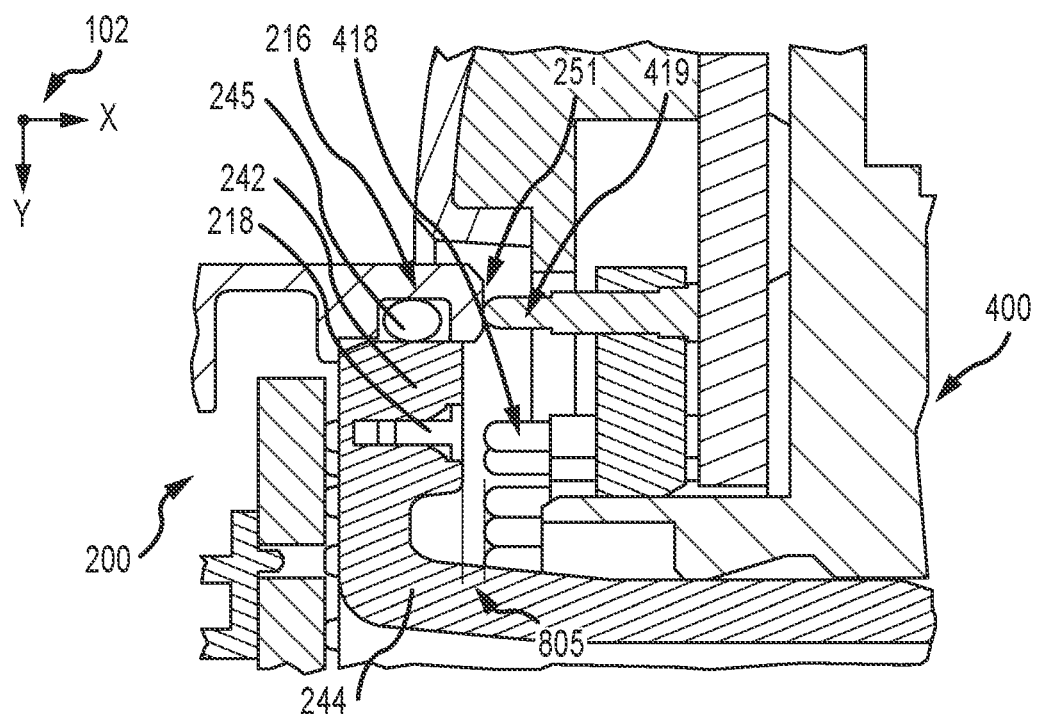
FIG. 8B is a cross-sectional diagram illustrating an example of a establishing the connected state between the endoscope connector and the endoscope adapter in accordance with example aspects of the present disclosure.
Figure 8C:
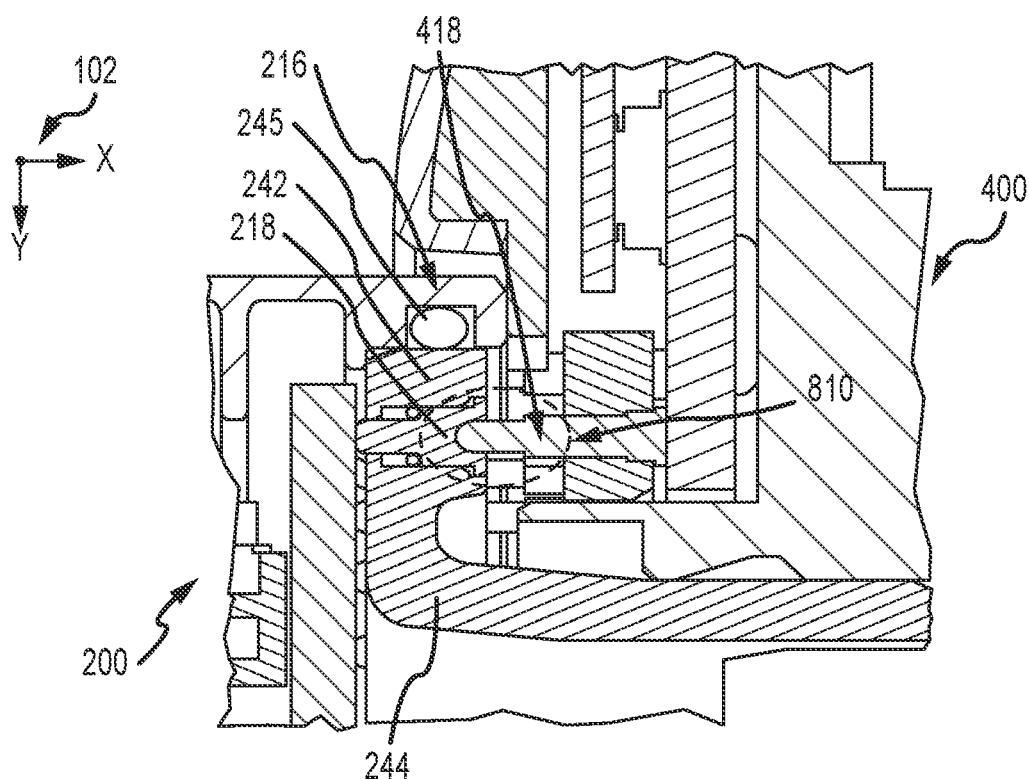
FIG. 8C is a cross-sectional diagram illustrating an example of the connected state between the endoscope connector and the endoscope adapter in accordance with example aspects of the present disclosure.

FIG. 8A is a cross-sectional diagram illustrating an example of a connected state between an endoscope connector 200 and an endoscope adapter 400 in accordance with example aspects of the present disclosure. FIG. 8B illustrates examples of establishing the connected state between the endoscope connector 200 and the endoscope adapter 400 in accordance with example aspects of the present disclosure. FIG. 8C illustrates an example of the connected state between the endoscope connector 200 and the endoscope adapter 400 in accordance with example aspects of the present disclosure.

Referring to the example of FIG. 8A, each of the electroconductive pins 418 and electroconductive pins 419 may include a shield portion 450 (also referred to herein as a ground contact, a shield contact, or the like) and a signal portion 451 (also referred to herein as a signal pin, a conductive portion, an electrically conductive portion, or the like). The electroconductive pins 419 may be referred to as shield pins. In some aspects, the shield portion 450 may be configured to retract and expose the signal portion 451. In some other aspects, the shield portion 450 may have a fixed position (e.g., be configured not to retract) such that the signal portion 451 is exposed.

For example, referring to the example electroconductive pin 419 illustrated in FIG. 8A, when coupling the endoscope connector 200 to the endoscope adapter 400, the electroconductive pin 419 may make contact (e.g., first contact) with a portion of the bushing 216. The shield portion 450 may retract (e.g., toward the proximal end of the endoscope adapter 400) in response to the contact, exposing a distal portion (e.g., a distal end) of the signal portion 451. In an example, the distal portion of the signal portion 451 may contact the bushing 216.

For example, the distal portion of the signal portion 451 may contact a portion 245 of the bushing 216. In an example, the portion 245 may be a grounded portion of the bushing 216 (e.g., electrically coupled to a reference ground of the endoscope connector 200 and/or the endoscope), and electroconductive pin 419 may be a ground pin electrically coupled to a reference ground of the endoscope adapter 400 and/or an external apparatus 300 (coupled to the endoscope adapter 400). In an example, the bushing 216 (or portion 245 in contact with the electroconductive pin 419) may provide an electrical connection to a chassis (ground connection) of the endoscope.

Accordingly, for example, referring to the example electroconductive pin 419 illustrated in FIG. 8A, when coupling the endoscope connector 200 to the endoscope adapter 400, the electroconductive pin 419 may be inserted into a gap (recess) between the bushing 216 and portion 242 (of the plug nose 205).

Optionally or alternatively, referring to the example electroconductive pin 419 illustrated in FIG. 8B, when coupling the endoscope connector 200 to the endoscope adapter 400, the gap (recess) illustrated in FIG. 8A may be omitted. For example, referring to FIG. 8B, the electroconductive pin 419 may make contact (e.g., first contact) with a portion (e.g., surface 251) of the bushing 216. In some aspects, when the electroconductive pin 419 makes contact (e.g., first contact) with the portion (e.g., surface 251) of the bushing 216, each electroconductive pin 418 may be a distance (e.g., an air gap 805 illustrated at FIG. 8B) from a corresponding electroconductive contact 218.

In an example, referring to the example electroconductive pin 418 illustrated in FIG. 8A and FIG. 8C, when coupling the endoscope connector 200 to the endoscope adapter 400, the shield portion 450 of the electroconductive pin 418 may make contact (e.g., first contact) with the bushing 216. The shield portion 450 may retract (e.g., toward the proximal end of the endoscope adapter 400) in response to the contact, exposing a distal portion (e.g., a distal end) of the signal portion 451. In an example, the distal portion (e.g., when exposed) of the signal portion 451 may contact the electroconductive contact 218. For example, the distal portion of the signal portion 451 may contact a signal portion (e.g., a connection contact, illustrated as connection contact portions 240 and 241) of the electroconductive contact 218. In an example, the signal portion of electroconductive contact 218 may be electrically coupled to a signal trace of a PCB of the endoscope connector 200, and electroconductive pin 418 may be a signal pin electrically coupled to a signal trace of a PCB of the endoscope adapter 400.

In an example, referring to FIG. 8C, contact is established between electroconductive contacts 218 and electroconductive pins 418, an example of which is indicated by connection 810.

FIGS. 9A and 9B are cross-sectional diagrams illustrating examples of a connected state between an endoscope connector 200 and an endoscope adapter 400 in accordance with example aspects of the present disclosure.

Referring to the example of FIG. 9A, aspects of electroconductive pins 418 in a compressed state is illustrated. For example, the electroconductive pins 418 may be in a compressed state as illustrated in FIG. 9A when the endoscope connector 200 and the endoscope adapter 400 are in an electrically and non-mechanically coupled state. Although two electroconductive pins 418 are illustrated in FIG. 9A, it is to be understood that the quantity of electroconductive pins 418 may be more than two (2), as according to the examples described herein. Further, aspects described herein with respect to the electroconductive pins 418 may be applied to the electroconductive pins 419 described herein.

In an example, each of the electroconductive pins 418 may generate a spring force when in a compressed state. In some aspects, a magnitude of a total spring force of the electroconductive pins 418 with respect to a magnitude of positive attraction forces (e.g., between the coupling element 220 and the coupling element 420 as described herein) may support reduced forces associated with inserting the endoscope connector 200 into the endoscope adapter 400 (e.g., low or zero insertion-force) and/or reduced forces associated with removing the endoscope connector 200 from the endoscope adapter 400 (e.g., disconnection force).

For example, aspects of the present disclosure may support implementations (e.g., for insertion, for removal, etc.) in which the magnitude of a total spring force of the electroconductive pins 418 is different from or equal to the magnitude of positive attraction forces (e.g., between the coupling element 220 and the coupling element 420 as described herein)

Referring to the example of FIG. 9B, example aspects of coupling element 220 and coupling element 420 are illustrated. For example, FIG. 9B illustrates an example in which the coupling element 220 includes magnets 231 (e.g., magnet 231-*a*, magnet 231-*b*) and the coupling element 420 includes magnets 431 (e.g., magnet 431, magnet 432), aspects of which have already been described herein.

Figure 10:
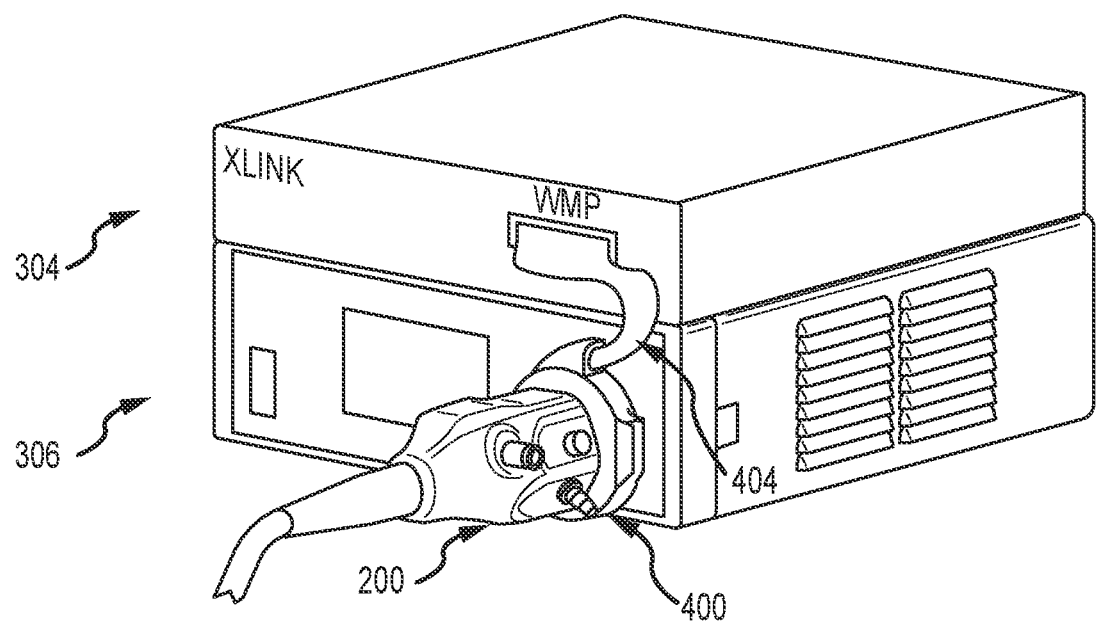
FIG. 10 illustrates an example of system in accordance with example aspects of the present disclosure.

FIG. 10 illustrates an example of system 100 in accordance with example aspects of the present disclosure. Referring to the example of FIG. 10, a cable core 404 from the endoscope adapter 400 on the external apparatus 306 (e.g., providing the light source) is connected to the external apparatus 304 (e.g., video processor).

Optionally or alternatively, signals communicated over the cable core 404 may be routed through external apparatus 306 (e.g., the light source), as previously described herein.

Optionally or alternatively, as previously illustrated and described herein, the light source and video processor may be integrated into a single device (e.g., external apparatus 300 illustrated in FIG. 1), and the cable core 404 may be omitted. For example, functionality (e.g., signal transmissions) supported by the cable core 404 may be implemented by example aspects of electroconductive contacts 218 and electroconductive pins 418 described herein.

Figure 11:
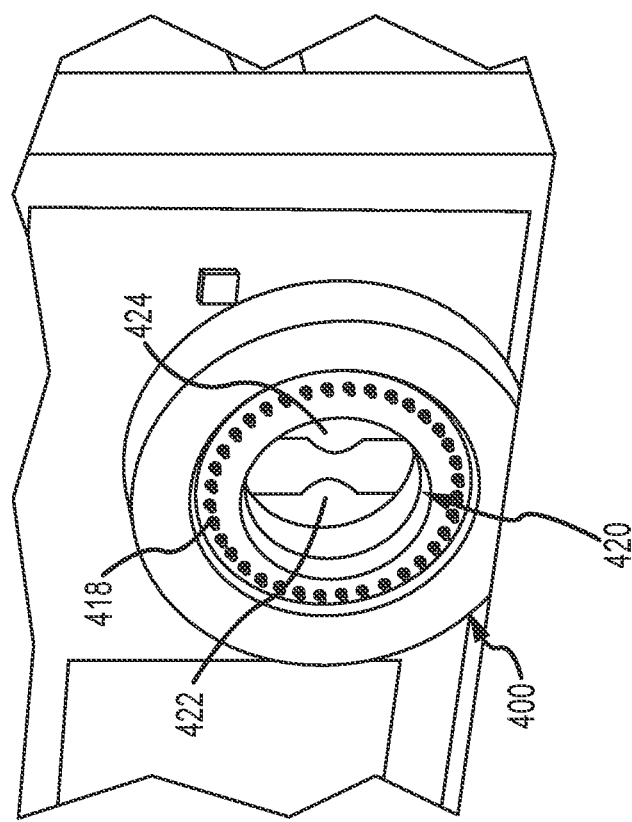
FIG. 11 illustrates an example of system in accordance with example aspects of the present disclosure.
Figure 11:
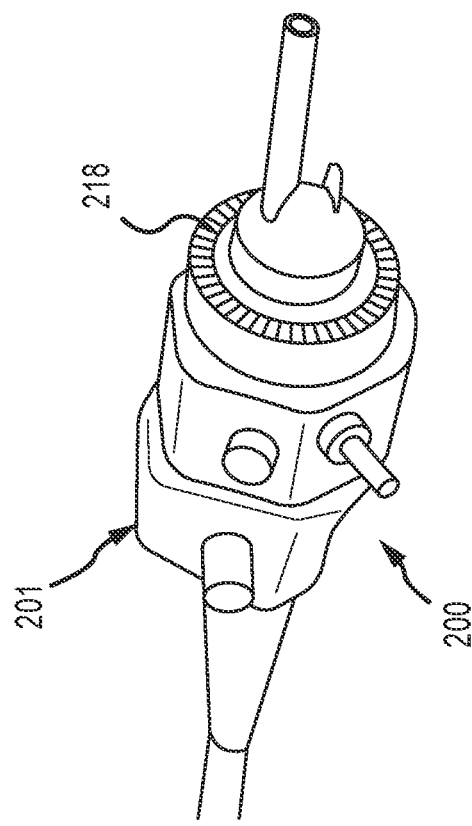

FIG. 11 illustrates an example of system 100 in accordance with example aspects of the present disclosure.

Referring to the example of FIG. 11, the electroconductive contacts 218 of the endoscope connector 200 are of a same shape (e.g., squircular shaped). Centers of the electroconductive contacts 218 are spaced apart from one another according to a fixed distance (in a direction perpendicular to the axial direction (e.g., X-axis) of the endoscope connector 200). The GI adapter 400 includes electroconductive pins 418. In some aspects, positions and/or spacing of the electroconductive pins 418 may correspond to (e.g., align with, in a direction parallel to the axial direction (e.g., X-axis) of the endoscope connector 200/GI adapter 400) positions and/or spacing of the electroconductive contacts 218 of the endoscope connector 200. In the example of FIG. 11, electroconductive contacts 218 and electroconductive pins 418 may support integrated power and data (e.g., video signal) transmission as described herein.

An example implementation of a coupling element 420 is illustrated which includes substantially planar surface 422 and substantially planar surface 424. The planar surface 422 and planar surface 424 may cover distal ends of magnets 431 and 432 (previously illustrated) of the endoscope adapter 400 in a direction parallel to the axial direction of the endoscope adapter 400.

Other example aspects of the endoscope connector 200 and GI adapter 400 already described herein are not repeated. For example, although not illustrated, the endoscope adapter 400 may include electroconductive pins 419 described herein.

Some aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

In the context of this document, a computer-readable storage medium may be any tangible medium that can contain or store a program for use by or in connection with an instruction execution system, apparatus, or device.

The terms "determine," "calculate," "compute," and variations thereof, as used herein, are used interchangeably and include any type of methodology, process, mathematical operation or technique.

A number of variations and modifications of the disclosure can be used. It would be possible to provide for some features of the disclosure without providing others.

As should be appreciated by one skilled in the art, aspects of the present disclosure have been illustrated and described herein in any of a number of patentable classes or context including any new and useful process, machine, manufacture, or composition of matter, or any new and useful improvement thereof.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more implementations, configurations, or aspects for the purpose of streamlining the disclosure. The features of the implementations, configurations, or aspects of the disclosure may be combined in alternate implementations, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed implementation, configuration, or aspect. Thus, the following claims are hereby incorporated into this Detailed Description, with each claim standing on its own as a separate preferred implementation of the disclosure.

Moreover, though the description of the disclosure has included description of one or more implementations, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative implementations, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Exemplary aspects are directed to an endoscope connector, including: a first portion having a first shape, the first portion including: a planar portion provided on at least a portion of the first shape, the planar portion including a substantially planar surface that may be parallel to an axial direction of the endoscope connector; and a first substantially planar surface perpendicular to the axial direction of the endoscope connector. The endoscope connector includes a first port protruding through the first planar surface. In some aspects, the first port may be a light port. The endoscope connector includes a second port protruding through the first planar surface. In some aspects, the second port may be an insufflation port. The endoscope connector includes a second portion having a circular shape, the second portion including: a second substantially planar surface perpendicular to the axial direction the endoscope connector; and a set of electroconductive contacts at least partially protruding through the second substantially planar surface. In some aspects, the set of electroconductive contacts are axially aligned with respect to the axial direction of the endoscope connector.

Any aspect optionally in conjunction with any other aspect wherein the planar portion is alignable with a corresponding planar portion of an external apparatus such that: the set of electroconductive contacts are axially aligned with a set of electroconductive pins of the external apparatus; and at least one port of the endoscope connector is axially aligned with a corresponding insertion port of the external apparatus.

Any aspect optionally in conjunction with any other aspect wherein the second portion includes a third portion including the second substantially planar surface; and at least a portion of each electroconductive contact of the set of electroconductive contacts is sealed in the third portion using a sealing element.

Any aspect optionally in conjunction with any other aspect wherein the sealing element includes at least one of: an O-ring seal; an adhesive material; a ceramic material; a glass material; a rubber material; and a urethane material.

Any aspect optionally in conjunction with any other aspect wherein at least a portion of the first substantially planar surface, at least a portion of the second substantially planar surface, or both, is substantially smooth.

Any aspect optionally in conjunction with any other aspect wherein the endoscope connector is non-mechanically attachable to an external apparatus.

Any aspect optionally in conjunction with any other aspect wherein the first portion includes at least one magnetic coupling element.

Any aspect optionally in conjunction with any other aspect wherein at least a portion of the first substantially planar surface includes the at least one magnetic coupling element.

Any aspect optionally in conjunction with any other aspect wherein at least a portion of the first substantially planar surface covers an end of the at least one magnetic coupling element.

Any aspect optionally in conjunction with any other aspect wherein the at least one magnetic coupling element is included in the first portion using insert injection molding; the at least one magnetic coupling element is sealed within the first portion using an O-ring seal; or both.

Any aspect optionally in conjunction with any other aspect wherein the at least one magnetic coupling element includes a ferromagnetic material.

Any aspect optionally in conjunction with any other aspect wherein the at least one magnetic coupling element includes a magnet.

Any aspect optionally in conjunction with any other aspect wherein the at least one magnetic coupling element includes an electromagnet.

Any aspect optionally in conjunction with any other aspect wherein the first port extends parallel to the axial direction of the endoscope connector; the second port extends parallel to the axial direction of the endoscope connector; and at least one dimension of the second port is smaller than a corresponding dimension of the first port.

Any aspect optionally in conjunction with any other aspect wherein the set of electroconductive contacts are electrically conductive with a set of electrically conductive pins of an external apparatus.

Any aspect optionally in conjunction with any other aspect wherein the set of electroconductive contacts are of a same shape; and the set of electroconductive contacts are spaced apart from one another according to a fixed distance.

Any aspect optionally in conjunction with any other aspect wherein the endoscope connector communicates data with an external apparatus via at least one first electroconductive contact of the set of electroconductive contacts; and the endoscope connector receives power from the external apparatus via at least one second electroconductive contact of the set of electroconductive contacts.

Any aspect optionally in conjunction with any other aspect wherein the first shape includes: a circular shape; a polygonal shape; a squircular shape; or a combination thereof.

Exemplary aspects are directed to an endoscope adapter, including: at least one magnetic coupling element; and a first substantially planar surface covering an end of the at least one magnetic coupling element. In some aspects, the substantially planar surface is perpendicular to an axial direction of the endoscope adapter. The endoscope adapter includes a second substantially planar surface perpendicular to the axial direction of the endoscope adapter. The endoscope adapter includes a set of electroconductive pins protruding through the second substantially planar surface. In some aspects, the set of electroconductive pins are axially aligned with respect to the axial direction of the endoscope adapter.

Aspects of the endoscope adapter optionally include a planar portion including a substantially planar surface that is parallel to the axial direction of the endoscope adapter. In some aspects, the planar portion is alignable with a corresponding planar portion of an endoscope connector such that: the set of electroconductive pins are axially aligned with a set of electroconductive contacts of the endoscope connector; and at least one insertion port of the endoscope adapter is axially aligned with a corresponding port of the endoscope connector.

Aspects of the endoscope adapter optionally include a planar portion including a third substantially planar surface that is perpendicular to the axial direction of the endoscope adapter. In some aspects, a first distance between the first substantially planar surface and a distal end of the endoscope adapter is different from a second distance between the third substantially planar surface and the distal end.

Aspects of the above endoscope adapter optionally include a second set of second electroconductive pins protruding through the second substantially planar surface. In some aspects, the set of second electroconductive pins are axially aligned with respect to the axial direction of the endoscope adapter; and a first distance between at least one electroconductive pin of the set of electroconductive pins and a central axis of the endoscope adapter is different from a second distance between at least one second electroconductive pin of the set of second electroconductive pins and the central axis of the endoscope adapter.

Aspects of the above endoscope adapter optionally include wherein the set of electroconductive pins produce a force that is opposite an attraction force associated with the at least one magnetic coupling element. In some aspects, the force produced by the set of electroconductive pins and the attraction force associated with the at least one magnetic coupling element are parallel to the axial direction of the endoscope adapter.

Aspects of the above endoscope adapter optionally include wherein the endoscope adapter is non-mechanically attachable to an endoscope connector.

Aspects of the above endoscope adapter optionally include a first insertion port and a second insertion port. In some aspects, a diameter of the first insertion port is perpendicular to the axial direction of the endoscope adapter. In some aspects, a diameter of the second insertion port is perpendicular to the axial direction of the endoscope adapter. In some aspects, the diameter of the second insertion port is smaller than the diameter of the first insertion port.

Aspects of the above endoscope adapter optionally include wherein light emitted by a light source is communicable via the first insertion port; and fluid provided by a fluid source is communicable via the second insertion port. In some aspects, the set of electroconductive pins are electrically conductive with a set of electroconductive contacts of an endoscope connector.

Aspects of the above endoscope adapter optionally include wherein the set of electroconductive pins are of a same shape; and the set of electroconductive pins are spaced apart from one another according to a fixed distance.

Aspects of the above endoscope adapter optionally include wherein the endoscope adapter communicates data with an endoscope connector via at least one first electroconductive pin of the set of electroconductive pins; and the endoscope adapter transmits power to the endoscope connector via at least one second electroconductive pin of the set of electroconductive pins.

Aspects of the above endoscope adapter optionally include wherein the at least one magnetic coupling element includes a magnet.

Aspects of the above endoscope adapter optionally include wherein the at least one magnetic coupling element includes an electromagnet.

Aspects of the above endoscope adapter optionally include wherein the at least one magnetic coupling element includes a ferromagnetic material Exemplary aspects are directed to a system including: an endoscope connector including a first portion having a first shape, the first portion including: a first planar portion that is parallel to an axial direction of the endoscope connector; and at least one first magnetic coupling element. The system includes an endoscope adapter including a second planar portion, the second planar portion including: a substantially planar surface that is parallel to an axial direction of the endoscope adapter; and at least one second magnetic coupling element. In some aspects, the endoscope connector is non-mechanically attachable to endoscope adapter using the at least one first magnetic coupling element and the at least one second magnetic coupling element.

Aspects of the above system optionally include wherein the first planar portion is alignable with the second planar portion such that: a set of electroconductive contacts of the endoscope connector are axially aligned with a set of electroconductive pins of the endoscope adapter; and at least one port of the endoscope connector is axially aligned with a corresponding insertion port of the endoscope adapter.

Aspects of the above system optionally include wherein the at least one first magnetic coupling element includes a ferromagnetic material; and the at least one second magnetic coupling element includes at least one magnet.

Aspects of the above system include wherein the at least one first magnetic coupling element includes at least one first magnet; and the at least one second magnetic coupling element includes at least one second magnet.

Aspects of the above system optionally include wherein the at least one first magnetic coupling element includes at least one first magnet; and the at least one second magnetic coupling element includes at least one second magnet.

Aspects of the above system optionally include a light source. In some aspects, light generated by the light source is communicable over a first input port included in the endoscope connector.

Aspects of the above system optionally include a fluid source. In some aspects, fluid output from the fluid source is communicable over a second input port included in the endoscope connector.

Aspects of the above system optionally include a video processor. In some aspects, signals are communicable to the video processor over a set of electroconductive contacts of the endoscope connector and a set of electroconductive pins of the endoscope adapter.

Aspects of the above system optionally include a first apparatus including the light source; and a second apparatus including the video processor.

Aspects of the above system optionally include an apparatus including the light source and the video processor.

Aspects of the above endoscope connector, endoscope adapter, and/or system include:

Any one or more of the above aspects as substantially disclosed herein.

Any one or more of the aspects as substantially disclosed herein, optionally in combination with any one or more other aspects as substantially disclosed herein.

One or means adapted to perform any one or more of the above aspects as substantially disclosed herein.

Any one or more of the features disclosed herein.

Any one or more of the features as substantially disclosed herein.

Any one or more of the features as substantially disclosed herein in combination with any one or more other features as substantially disclosed herein.

Any one of the aspects/features in combination with any one or more other aspects/features.

Use of any one or more of the aspects or features as disclosed herein.

It is to be appreciated that any feature described herein can be claimed in combination with any other feature(s) as described herein, regardless of whether the features come from the same described implementation.

It is to be appreciated that any feature described herein may be implemented as an optional feature. In some aspects, it is to be appreciated that any feature described herein may be omitted. In some aspects, it is to be appreciated that any feature described herein may be combined with any other feature(s) described herein.

As used herein, the singular forms "a," "an," and "the" are intended to include the plural forms as well, unless the context clearly indicates otherwise. It will be further understood that the terms "include," "including," "includes," "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. An endoscope connector, comprising:
a first portion having a first shape, the first portion comprising:

a planar portion provided on at least a portion of the first shape, the planar portion comprising a planar surface that is parallel to an axial direction of the endoscope connector;
at least one magnetic coupling element; and
a first planar surface perpendicular to the axial direction of the endoscope connector;
a first port protruding through the first planar surface, wherein the first port is a light port;
a second port protruding through the first planar surface, wherein the second port is an insufflation port; and
a second portion having a circular shape, the second portion comprising:
a second planar surface perpendicular to the axial direction the endoscope connector; and
a set of electroconductive contacts at least partially protruding through the second planar surface, wherein the set of electroconductive contacts are axially aligned with respect to the axial direction of the endoscope connector.

2. The endoscope connector of claim 1, wherein the planar portion is alignable with a corresponding planar portion of an external apparatus such that:
the set of electroconductive contacts are axially aligned with a set of electroconductive pins of the external apparatus; and
at least one port of the endoscope connector is axially aligned with a corresponding insertion port of the external apparatus.

3. The endoscope connector of claim 1, wherein:
the second portion comprises a third portion including the second planar surface; and
at least a portion of each electroconductive contact of the set of electroconductive contacts is sealed in the third portion using a sealing element.

4. The endoscope connector of claim 3, wherein the sealing element comprises at least one of:
an O-ring seal;
an adhesive material;
a ceramic material;
a glass material;
a rubber material; and
a urethane material.

5. The endoscope connector of claim 1, wherein at least a portion of the first planar surface, at least a portion of the second planar surface, or both, is smooth.

6. The endoscope connector of claim 1, wherein the endoscope connector is non-mechanically attachable to an external apparatus.

7. The endoscope connector of claim 1, wherein the first portion comprises in a portion thereof the at least one magnetic coupling element.

8. The endoscope connector of claim 7, wherein at least a portion of the first planar surface comprises the at least one magnetic coupling element.

9. The endoscope connector of claim 7, wherein at least a portion of the first planar surface covers an end of the at least one magnetic coupling element.

10. The endoscope connector of claim 7, wherein one or more of:
the at least one magnetic coupling element is included in the first portion using insert injection molding; and
the at least one magnetic coupling element is sealed within the first portion with an O-ring seal.

11. The endoscope connector of claim 7, wherein the at least one magnetic coupling element comprises a ferromagnetic material.

12. The endoscope connector of claim 7, wherein the at least one magnetic coupling element comprises a magnet.

13. The endoscope connector of claim 7, wherein the at least one magnetic coupling element comprises an electromagnet.

14. The endoscope connector of claim 1, wherein:
the first port extends parallel to the axial direction of the endoscope connector;
the second port extends parallel to the axial direction of the endoscope connector; and
at least one dimension of the second port is smaller than a corresponding dimension of the first port.

15. The endoscope connector of claim 1, wherein:
the set of electroconductive contacts are configured to be electrically conductive with a set of electrically conductive pins of an external apparatus.

16. The endoscope connector of claim 1, wherein:
the set of electroconductive contacts are of a same shape; and
the set of electroconductive contacts are spaced apart from one another according to a fixed distance.

17. The endoscope connector of claim 1, wherein:
the endoscope connector is configured to communicate data with an external apparatus via at least one first electroconductive contact of the set of electroconductive contacts; and
the endoscope connector is configured to receive power from the external apparatus via at least one second electroconductive contact of the set of electroconductive contacts.

18. The endoscope connector of claim 1, wherein the first shape comprises:
a circular shape;
a polygonal shape;
a squircular shape; or
a combination thereof.

* * * * *

UNITED STATES PATENT AND TRADEMARK OFFICE
CERTIFICATE OF CORRECTION

| | | |
|---|---|---|
| PATENT NO. | : 12,274,417 B2 | Page 1 of 1 |
| APPLICATION NO. | : 18/519630 | |
| DATED | : April 15, 2025 | |
| INVENTOR(S) | : Anina Cooter et al. | |

It is certified that error appears in the above-identified patent and that said Letters Patent is hereby corrected as shown below:

On the Title Page

Item (72) "Inventors" please delete "Evan M. Leingang, Plymouth, NM" and insert --Evan M. Leingang, Plymouth, MN--, therefore.

Signed and Sealed this
Twentieth Day of May, 2025

Coke Morgan Stewart
*Acting Director of the United States Patent and Trademark Office*